(12) United States Patent
Sutherland et al.

(10) Patent No.: US 9,999,507 B2
(45) Date of Patent: Jun. 19, 2018

(54) PERCUTANEOUS VALVE REPAIR BY RESHAPING AND RESIZING RIGHT VENTRICLE

(71) Applicant: Mitralign, Inc., Tewksbury, MA (US)

(72) Inventors: Michael Sutherland, Pelham, NH (US); Christopher Lee, Tewksbury, MA (US); Richard Morrill, North Billerica, MA (US); Steven Cahalane, Pelham, NH (US)

(73) Assignee: MITRALIGN, INC., Tewksbury, MA (US)

( * ) Notice: Subject to any disclaimer, the term of this patent is extended or adjusted under 35 U.S.C. 154(b) by 0 days. days.

(21) Appl. No.: 14/314,187

(22) Filed: Jun. 25, 2014

(65) Prior Publication Data

US 2014/0379006 A1 Dec. 25, 2014

Related U.S. Application Data

(60) Provisional application No. 61/838,873, filed on Jun. 25, 2013.

(51) Int. Cl.
*A61F 2/24* (2006.01)
*A61B 17/04* (2006.01)
(52) U.S. Cl.
CPC ........ *A61F 2/2487* (2013.01); *A61B 17/0401* (2013.01); *A61B 2017/0409* (2013.01);
(Continued)

(58) Field of Classification Search
CPC .... A61F 2/2442; A61F 2/2445; A61F 2/2454; A61F 2/2457
See application file for complete search history.

(56) References Cited

U.S. PATENT DOCUMENTS 5,332,402 A 7/1994 Teitelbaum
5,364,408 A 11/1994 Gordon
(Continued)

FOREIGN PATENT DOCUMENTS

CN 102869318 1/2013
WO WO 2008/112740 9/2008
(Continued)

*Primary Examiner* — Leslie Lopez
(74) *Attorney, Agent, or Firm* — Leason Ellis LLP

(57) ABSTRACT

The present teachings provide devices and methods of treating a tricuspid valve regurgitation. Specifically, one aspect of the present teachings provides devices and methods for reshaping and resizing the right ventricle by reducing the distances between two papillary muscles. Another aspect of the present teachings provides devices and methods for reshaping and resizing the right ventricle by reducing the distances along the right ventricle wall. Another aspect of the present teachings provides devices and methods for reshaping and resizing the right ventricle by reducing the distance between the distance of right ventricle outflow track and the right ventricle wall. Another aspect of the present teachings provides devices and methods for reshaping and resizing the right ventricle by changing the right ventricle sphericity index. Another aspect of the present teachings provides devices and methods for reshaping and resizing the right ventricle by reducing the tricuspid valve tethering height.

14 Claims, 28 Drawing Sheets

(52) U.S. Cl.
CPC ..... *A61B 2017/0417* (2013.01); *A61F 2/2427* (2013.01); *A61F 2/2439* (2013.01); *A61F 2002/249* (2013.01); *A61F 2220/0075* (2013.01)

(56) References Cited

U.S. PATENT DOCUMENTS

| | | | |
|---|---|---|---|
| 5,733,331 A * | 3/1998 | Peredo | A61F 2/2412 623/2.13 |
| 5,810,746 A | 9/1998 | Goldstein et al. | |
| 6,048,351 A | 4/2000 | Gordon | |
| 6,629,534 B1 * | 10/2003 | St Goar | A61B 17/0469 128/898 |
| 7,431,726 B2 | 10/2008 | Spence et al. | |
| 8,029,556 B2 | 10/2011 | Rowe | |
| 8,382,829 B1 | 2/2013 | Call et al. | |
| 8,475,525 B2 | 7/2013 | Maisano et al. | |
| 8,845,717 B2 | 9/2014 | Khairkhahan et al. | |
| 8,888,843 B2 | 11/2014 | Khairkhahan et al. | |
| 8,961,594 B2 | 2/2015 | Maisano et al. | |
| 8,961,596 B2 | 2/2015 | Maisano et al. | |
| 2002/0107531 A1 | 8/2002 | Schreck et al. | |
| 2003/0120340 A1 | 6/2003 | Liska et al. | |
| 2003/0199974 A1 | 10/2003 | Lee | |
| 2004/0162610 A1 | 8/2004 | Liska et al. | |
| 2004/0225233 A1 | 11/2004 | Frankowski et al. | |
| 2005/0119734 A1 | 6/2005 | Spence et al. | |
| 2005/0267571 A1 | 12/2005 | Spence | |
| 2006/0229708 A1 * | 10/2006 | Powell | A61B 17/00234 623/1.24 |
| 2007/0010857 A1 | 1/2007 | Sugimoto et al. | |
| 2007/0112425 A1 | 5/2007 | Schaller | |
| 2008/0086164 A1 | 4/2008 | Rowe | |
| 2009/0076547 A1 | 3/2009 | Sugimoto | |
| 2009/0093670 A1 | 4/2009 | Annest et al. | |
| 2009/0292353 A1 | 11/2009 | Yoganathan et al. | |
| 2010/0063586 A1 * | 3/2010 | Hasenkam | A61B 17/0401 623/2.37 |
| 2010/0070028 A1 | 3/2010 | Sugimoto | |
| 2010/0210899 A1 * | 8/2010 | Schankereli | A61B 17/00234 600/37 |
| 2010/0292785 A1 | 11/2010 | Seguin et al. | |
| 2011/0015476 A1 | 1/2011 | Franco | |
| 2011/0060407 A1 * | 3/2011 | Ketai | A61B 17/00234 623/2.37 |
| 2011/0071626 A1 * | 3/2011 | Wright | A61B 17/00234 623/2.37 |
| 2011/0184510 A1 | 7/2011 | Maisano et al. | |
| 2012/0029627 A1 | 2/2012 | Salahieh et al. | |
| 2012/0035712 A1 | 2/2012 | Maisano et al. | |
| 2012/0203336 A1 | 8/2012 | Annest | |
| 2012/0310840 A1 | 12/2012 | Colombo et al. | |
| 2013/0018459 A1 | 1/2013 | Maisano et al. | |
| 2013/0046380 A1 | 2/2013 | Maisano et al. | |
| 2014/0114390 A1 | 4/2014 | Tobis et al. | |
| 2014/0243859 A1 | 8/2014 | Robinson | |
| 2014/0243894 A1 | 8/2014 | Groothuis et al. | |
| 2014/0350662 A1 | 11/2014 | Vaturi | |
| 2015/0025553 A1 | 1/2015 | Del Nido et al. | |
| 2015/0112429 A1 | 4/2015 | Khairkhahan et al. | |
| 2015/0119936 A1 | 4/2015 | Gilmore et al. | |
| 2015/0119979 A1 | 4/2015 | Maisano et al. | |
| 2015/0164637 A1 | 6/2015 | Khairkhahan et al. | |

FOREIGN PATENT DOCUMENTS

| | | |
|---|---|---|
| WO | WO 2012/004679 | 1/2012 |
| WO | WO 2012/178115 | 12/2012 |
| WO | WO 2014/134183 | 9/2014 |

\* cited by examiner

RV sphericity index = b / a

PERCUTANEOUS VALVE REPAIR BY RESHAPING AND RESIZING RIGHT VENTRICLE

CROSS-REFERENCE TO RELATED APPLICATION

The present invention claims the benefit of U.S. patent application Ser. No. 61/838,873, filed Jun. 25, 2013, which is hereby incorporated by reference in its entirety.

TECHNICAL FIELD

The present teachings generally relate to percutaneous tricuspid valve repair by reshaping and resizing the right ventricle. Some embodiments of the present teachings relate to pulling one papillary muscle toward another, toward a septum, or toward a ventricular free wall percutaneously. Other embodiments of the present teachings relate to pulling a ventricular free wall toward a septum.

BACKGROUND

Tricuspid valve diseases relate to conditions in which the valve between the two right heart chambers (i.e., the right ventricle and the right atrium) doesn't function properly and they often occur with other heart valve problems. An example of tricuspid valve diseases is tricuspid valve regurgitation, where the tricuspid valve doesn't close properly and blood flows back into the right atrium. Uncorrected, functional tricuspid regurgitation has serious long-term morbidity and mortality. Another example is tricuspid valve stenosis where the tricuspid valve is narrowed, which reduces the amount of blood flowing into the right ventricle. Yet another example is tricuspid atresia, a congenital heart disease, where a solid wall of tissues blocks the blood from flowing between the two right heart chambers. Yet another example is the Ebstein's anomaly where a malformed tricuspid valve situates at a position lower than the normal position in the right ventricle, causing blood to flow back into the right atrium. There are other tricuspid valve diseases generally known to a person with ordinary skill in the art and these tricuspid valve diseases are also included in the present teachings.

A tricuspid valve disease can be corrected by an annuloplasty ring. In some instances, this device is preferred for surgically repairing a defect tricuspid valve. An annuloplasty ring is an anatomically-correct three-dimensional (3D) ring and can flexibly conform to the heart valve opening. This ring is implanted into a defect tricuspid valve and reduces the valve opening. Properly implanted, an annuloplasty ring allows the valve to open and close properly.

A tricuspid valve repair surgery can be done in one of the following two ways: a minimally invasive surgery or an open-heart surgery. A minimally invasive method involves making a small upper or lower chest incision and inserting a valve repairing system/device percutaneously. After the valve is repaired, the incision is closed with dissolving sutures. Advantages of a minimally invasive approach include a shorter recovery time, less post-operation pain, and earlier return to work and normal daily activities.

SUMMARY

One aspect of the present teachings provides a device for reshaping and resizing the right ventricle. This device comprises a first tissue anchor attached to a first tension member and adapted to be secured to a first treatment location, a second tissue anchor attached to a second tension member and adapted to be secured to a second treatment location, and a lock configured to fasten both the first and second tissue anchors and adapted to retain tension to at least one of the first and second tension members. In one embodiment, the first or the second tissue anchor of the device is adapted to be secured to a papillary muscle. In another embodiment, the first or the second tissue anchor of the device is adapted to be secured to the right ventricle wall. In another embodiment, the first or the second tissue anchor is adapted to be secured to pulmonary artery. In another embodiment, the first or the second tissue anchor is adapted to be secured to right ventricle outflow track.

In another aspect of the present teachings, the device comprises a third tissue anchor attached to a third tension member and adapted to be secured to a third treatment location. In such embodiment, the device further comprises a lock fastened to the first, second, and third tissue anchors, and adapted to retain tension to at least one of the first, second and third tension members.

In some aspect of the present teachings, the lock of the device reduces the distance between the first treatment location and the second treatment location. In another aspect of the present teachings, the device is adapted to be percutaneously delivered and deployed.

Another aspect of the present teachings provides a method for reshaping and resizing the right ventricle. The method comprises securing a first papillary muscle with a first tissue anchor, wherein the first tissue anchor attaches to a first tension member, securing a second papillary muscle with a second tissue anchor, wherein the second tissue anchor attaches to a second tension member, and tensioning at least one of the first and second tension members so that the first papillary muscle is moved towards the second papillary muscle by a desired distance.

Another aspect of the present teachings provides a method for reshaping and resizing the right ventricle. The method comprises securing the right ventricle wall with a first tissue anchor at a first treatment location, wherein the first tissue anchor attaches to a first tension member, securing right ventricle wall with a second tissue anchor at a second treatment location, wherein the second tissue anchor attaches to a second tension member, and tensioning at least one of the first and second tension members so that the first and second treatment locations are moved towards each other by a desired distance.

Another aspect of the present teachings provides a method for reshaping and resizing the right ventricle. The method comprises securing a first tissue anchor inside the pulmonary artery, wherein the first tissue anchor attaches to a first tension member, securing a second tissue anchor to right ventricle wall away from the first tissue anchor inside the pulmonary artery by a first distance, wherein the second tissue anchor attaches to a second tension member, and tensioning at least one of the first and second tension members so that the first tissue anchor is away from the second tissue anchor by a second distance. Such second distance is smaller than the first distance where the first tissue anchor is away from the second tissue anchor.

DETAILED DESCRIPTION

Figure 1:
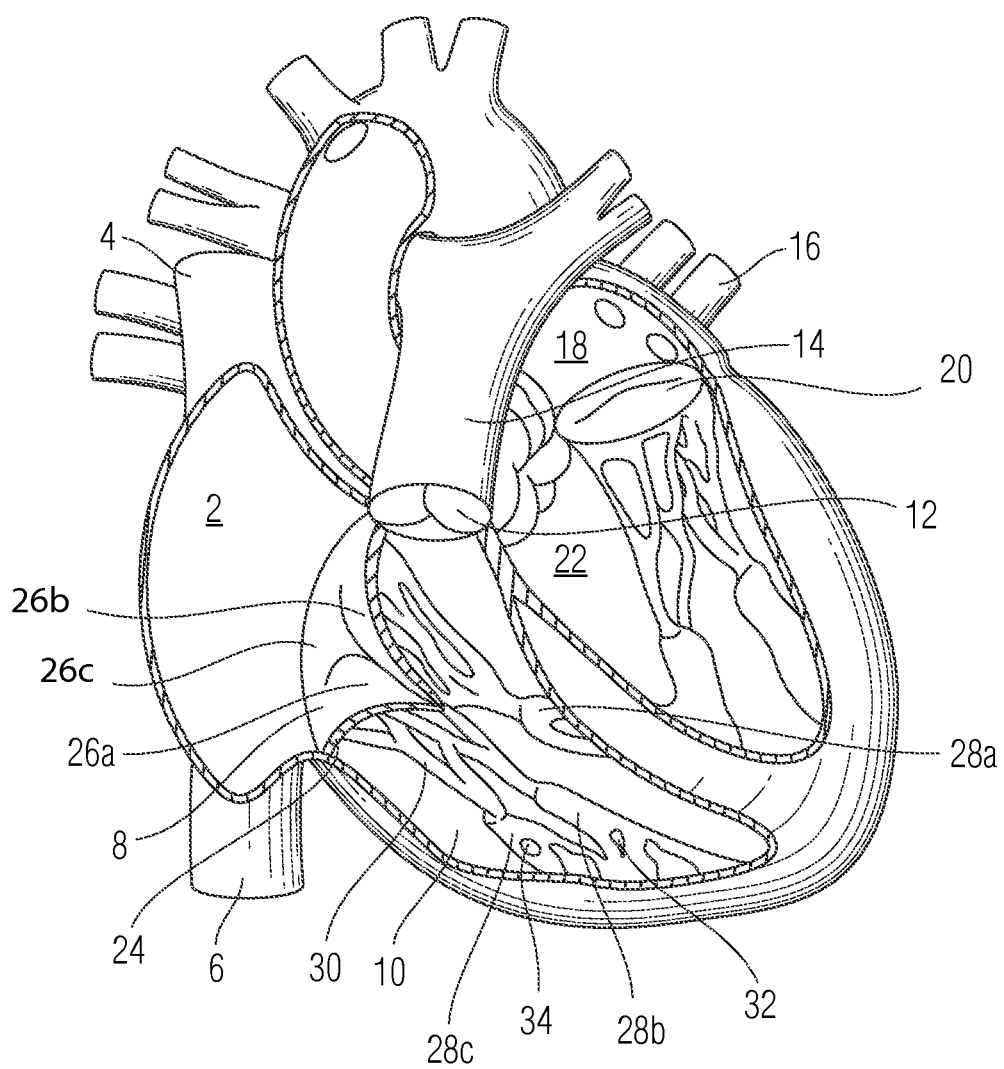
FIG. 1 is a perspective view of a heart anatomy.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a catheter, a hollow needle, a tube, a vein, an artery, a blood vessel, a capillary, an intestine, and the like.

As used herein, the term "proximal" shall mean close to the operator (less into the body) and "distal" shall mean away from the operator (further into the body). In positioning a medical device inside a patient, "distal" refers to the direction away from a catheter insertion location and "proximal" refers to the direction close to the insertion location.

As used herein, the term "sheath" may also be described as a "catheter" and, thus, these terms can be used interchangeably.

While the description above refers to a suture, other terms, for example, a wire, a strand, a cord, a fiber, a yarn, a filament, a cable, a thread, a string or the like, and these terms may be used interchangeably. One skilled in the art will also understand that certain metallic wires can also be used as the suture, or tension member, such as stainless steel wire, nitinol wire, etc. In addition, in some embodiments, each string, suture, filament, or tension member comprises one or more strings, sutures, filaments, or tension members. According to various embodiments, the suture or the tension member could be made from one or more of numerous materials, either polymeric or metallic. The polymeric suture or the tension member material can be polyglycolic acid (Biovek), polylactic acid, polydioxanone, and caprolactone, synthetics polypropylene, polyester or nylon etc. In another embodiments, other non-absorbable suture or tension member material, for example, special silk, can be used.

The following description refers to FIGS. 1 to 37. A person with ordinary skill in the art would recognize that the figures and description thereto refer to various embodiments of the present teachings and, unless indicated otherwise by their contexts, do not limit the scope of the attached claims to the figures and/or description thereto.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

According to some embodiments, the present teachings relate to devices and methods for treating a tricuspid regurgitation by reshaping and resizing the right ventricle (10). In one aspect of the present teachings, as illustrated in FIGS. 2-14 and FIGS. 21-32, the reshaping and resizing of the right ventricle (10) is achieved by pulling at least one papillary muscle toward another papillary muscle. In another aspect of the present teachings, as illustrated in FIGS. 15-20, the reshaping and resizing of the right ventricle (10) is achieved by pulling the right ventricle wall (200) toward the center of the ventricle. According to another aspect of the present teachings, as illustrated in FIGS. 33-37, the reshaping and resizing of the right ventricle (10) is achieved by pulling a right ventricle wall (200) toward the pulmonary valve (12).

FIG. 1 illustrates a cross-sectional view of the heart anatomy. In a normal heart function, deoxygenated blood from the body enters the right atrium (2) through either the superior vena cava (4) or the inferior vena cava (6). Upon filling the right atrium (2), the deoxygenated blood is pumped through the tricuspid valve (8) into the right ventricle (10). As the right ventricle (10) contracts, the deoxygenated blood is then pumped through the pulmonary valve (12) into the pulmonary arteries (14). Through the pulmonary arteries (14), the deoxygenated blood enters the lungs. The blood is oxygenated in the lungs, returns through the pulmonary veins (16), and enters the left atrium (18). The oxygenated blood is then pumped through the mitral valve (20) into the left ventricle (22). Upon filling the left ventricle (22), the blood is pumped through the aorta valve into the aorta, where it is distributed to the body.

The tricuspid valve complex consists of the annulus (24), leaflets (26a-c), papillary muscles (28a-c), and chordae tendinae (30). The tricuspid valve (8) lies between the right atrium (2) and the right ventricle (10), and is supported by the tricuspid annulus (24). The tricuspid annulus (24) separates the right atrium (2) from the right ventricle (10). The tricuspid valve (8) has three leaflets (26a-c) which are thin and membranous. As illustrated in FIG. 1. The three leaflets (26a-c) are the anterior (26c), septal (26b) and posterior leaflets (26a), with the anterior (26c) and the septal leaflets (26b) being the largest leaflets and the posterior leaflet (26a) the smallest.

The three tricuspid leaflets (26a-c), are connected to three papillary muscles (28a-c). The three tricuspid papillary muscles (28a-c) are the anterior (28c), posterior (28b), and septal (28a) papillary muscles, as illustrated in FIG. 1. The papillary muscles (28a-c) exhibit variability in size. The anterior (28c) and septal (28b) papillary muscles are the largest. The posterior papillary (28a) muscle is small and, at times, absent. Each leaflet (26a-c) has chordal (30) attachments to one or more papillary muscles (28a-c).

FIGS. 2-14 illustrate one aspect of the present teachings, where a first papillary muscle (26a) is secured to a first suture by a first tissue anchor (110), a second papillary muscle is secured to a second suture with a second tissue anchor, tension is applied to one or both sutures so that the first and the second papillary muscles are pulled close to each other, and a lock is used to maintain the tension on the first and second sutures. According to one embodiment of the preset teachings and as illustrated in FIG. 12, the sutures are secured to the papillary muscle by implanting a tissue anchor across the papillary muscles at or near the base.

Figure 2:
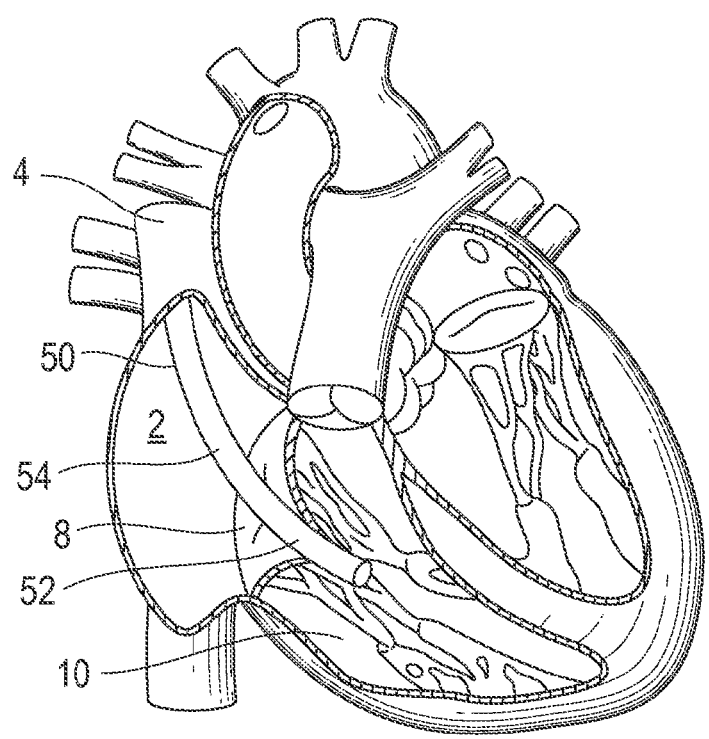
FIG. 2 is a perspective view of an exemplary guide percutaneously inserted into the right ventricle in accordance with the present teachings.

An exemplary method of the present teachings begins by percutaneously placing a guide (50) inside the right ventricle (2) from a suitable venous access site, as illustrated in FIG. 2. According to some embodiments, the venous access site is located near the jugular vein, superiorly, from the femoral vein, inferiorly, or from other suitable sites. According to some embodiments of the present teachings, as illustrated in FIG. 2, a suitable guide (50) is directed into the internal jugular vein, extends through the right brachiocephalic vein, the superior vena cava (4), and reaches the right atrium (2). The guide (50) is further extended distally, through the tricuspid valve (8), and reaches the right ventricle (10). As seen in FIG. 2, the distal end (52) of the guide (50) remains inside the right ventricle (10). The proximal end (not shown) of the guide (50) remains outside of the body. Although FIG. 2 shows the distal end (52) of the guide (50) inside the right ventricle (2), one skilled in the art should understand that the distal end of the guide could be kept inside the right atrium throughout the procedure. Alternatively, no guide is used for the procedure in the present teachings, other mechanism such as a guide wire could be used for maintaining the access. Additionally, although FIG. 2 shows that the access to the right ventricle starts from the jugular vein, through the right brachiocephalic vein, the superior vena cava (4), reaching the right atrium, one skilled in the art should understand that the access could also start from the femoral vein, to the inferior vena cava, and reaching the right atrium.

According to one embodiment of the present teachings, the guide (50) has an axial lumen (54) extending from its proximal end through its entire length to its distal end (52). This axial lumen (54) of the guide (50) serves as a conduit for one or more delivery catheters access the right ventricle (10). According to one embodiment, the guide (50) remains in place as illustrated in FIG. 2 during the entire procedure, and to be removed when the entire procedure is completed. According to another embodiment, the guide (50) is sometimes replaced by a guide wire keeping the percutaneous access to the right ventricle (10). According to some embodiments, the guide (50) could be up to a 20 French (F) sheath. According to some embodiments, the guide (50) could be a single lumen sheath that can accommodate all subsequent delivery catheters sliding therein. Alternatively, the guide (50) could be a multi-lumen sheath, where each lumen accommodates a delivery catheter separately. It, however, should be appreciated by persons of ordinary skill in the art that the size and the exact configuration of the guide (50) should not be viewed as limiting to the scope of the present teachings.

In various embodiments, a percutaneous resizing and reshaping of the right ventricle (10) starts with securing a first papillary muscle to a first suture with a first tissue anchor (110). FIGS. 3-8 illustrate some embodiments where a first tissue piercing wire is placed across the first treatment location (68), followed by deploying a first tissue anchor (110) across the first treatment location (68).

Figure 3:
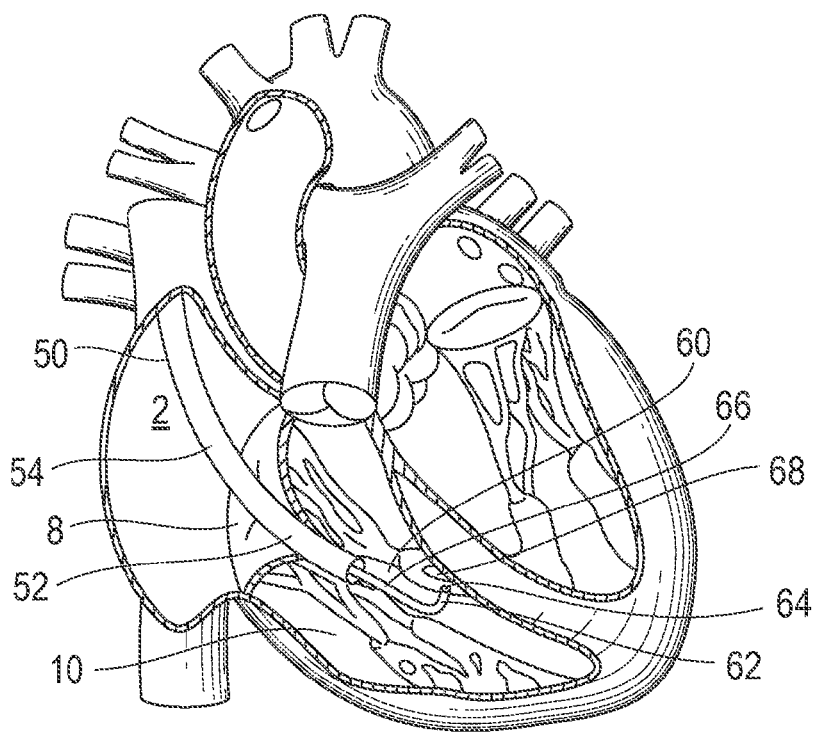
FIG. 3 is a perspective view of an exemplary wire delivery catheter directed into the right ventricle in accordance with the present teachings.
Figure 4:
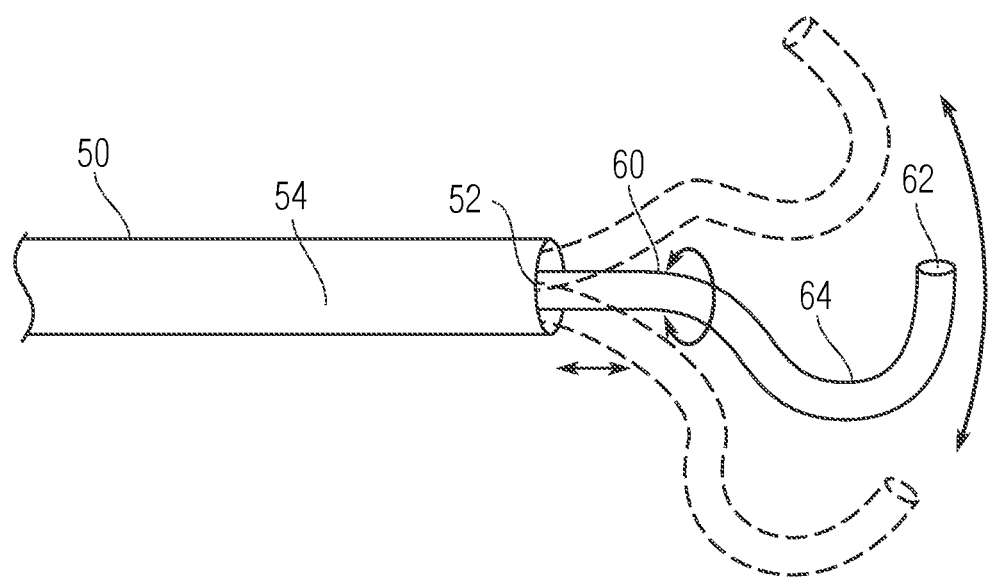
FIG. 4 is a perspective view of an exemplary wire delivery catheter in accordance with the present teachings.

FIG. 3 illustrates an embodiment of the present teachings where a wire delivery catheter (60) is directed into the right ventricle (10). In one embodiment, a wire delivery catheter (60) has a proximal end (not shown), a distal end (62), with a central lumen (66) extending from the proximal end to the distal end (62). In one embodiment, a wire delivery catheter (60) is inserted from the proximal end of the guide (50) through the lumen (54) of the guide (50) and reaches the right ventricle (10). FIG. 3 illustrates the distal end (62) of the first wire delivery catheter (60) extends beyond the distal end (52) of the guide (50), and inside the right ventricle (10).

According to one embodiment of the present teachings, as illustrated in FIG. 3, the distal end portion (64) of the first wire delivery catheter (60) bends radially away from the longitudinal axis of the first wire delivery catheter (60), assuming a curved profile. According to some embodiments, the curved profile of the distal end portion (64) of the first wire delivery catheter (60) is in the shape of a hook, the letter "J", or any curvature. According to the embodiments of the teachings, a clinician manipulates the distal end (62) of the first wire delivery catheter (60) from outside of the body, getting around critical anatomy inside the right ventricle (10), and accurately positioning the distal end (62) of the first wire delivery catheter (60) against the first treatment location (68), as illustrated in FIG. 3. In an alternative embodiment, the first wire delivery catheter (60) is configured in such a way that as the curved distal end portion (64) touches the free wall of the right ventricle (10), the distal end (62) of the first wire delivery catheter (60) would be against the first treatment location (68).

According to some embodiments, the distal end portion (64) of the first wire delivery catheter (60) has a preformed curve, such that as the distal end portion (64) of the first wire delivery catheter (60) leaves the constraint of the guide (50), the distal end portion (64) of the first wire delivery catheter (60) assumes its curved profile. According to some other embodiments, the first wire delivery catheter (60) has a deflectable distal end portion (64), which is actuated by a clinician to form the curved profile. One skilled in the art would understand that such an actuation can be accomplished by many mechanisms known in the field. According to some embodiments, the first wire delivery catheter (60) can be extended distally, retracted proximally, turned axially, and its distal end can pivot radially as shown by the double-headed arrows in FIG. 4.

According to one embodiment of the present teachings, the first treatment location (68) is identified and confirmed by injecting a contrast dye inside the right ventricle (10). Alternatively, the location can be identified by incorporating one or more segments or markers designed for visibility under imaging modalities such as fluoroscopy, ultrasound, MRI. In various embodiments, the contrast dye and/or the radio-opaque marker renders all or portions of the inside of the right ventricle (10) visible under a radiographic imaging equipment such as X-ray, magnetic resonance, ultrasound, fluoroscope, or other imaging techniques. By visualizing the inside of the right ventricle (10), a clinician can identify and confirm the treatment location from outside of the body.

According to some embodiments, the distal end (62) of the first wire delivery catheter (60) is adapted to locate and contact a first treatment location (68), as shown in FIG. 3. According to one embodiment, although not specifically shown in FIG. 3, the first treatment location is at or near the base of the posterior papillary muscle (26a). Alternatively, the first treatment location is at or near the middle portion of the posterior papillary muscle (26a). According to another embodiment, the first treatment location is at or near the base of the anterior papillary muscle (26c). Alternatively, the first treatment location is at or near the middle portion of the anterior papillary muscle (26c). In some embodiments, the first treatment location is near the trabeculae carneae (32) at the base of the posterior or anterior papillary muscle (26a, 26c). One skilled in the art would understand that other locations along, within, or around the papillary muscles can also be used as a first treatment location.

Figure 5:
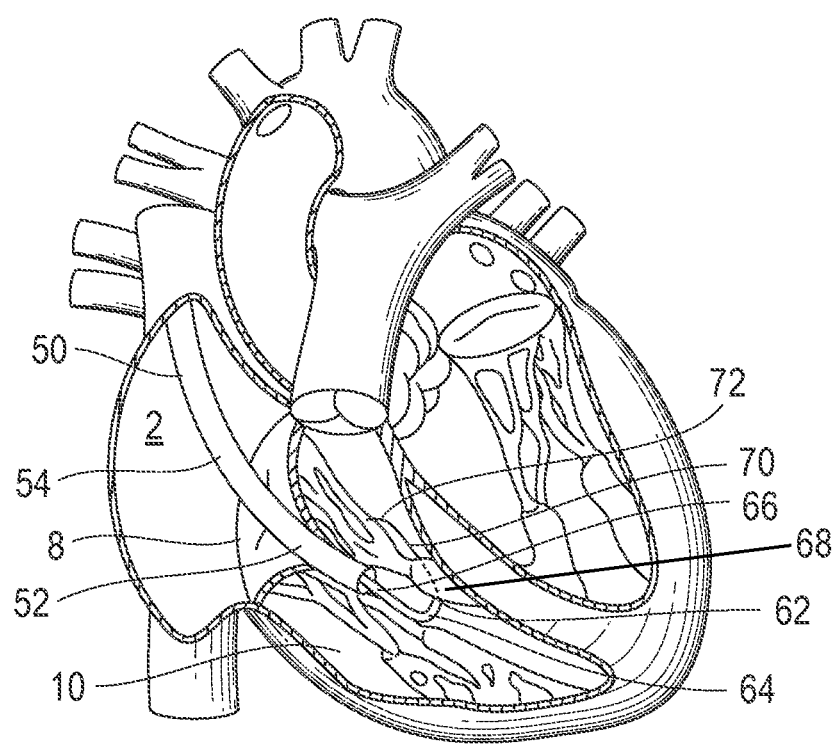
FIG. 5 is a perspective view of an exemplary wire delivery catheter delivering an exemplary tissue piercing wire across the tissue at a treatment location in accordance with the present teachings.

As the distal end (62) of the first wire delivery catheter (60) positioned against the first treatment location (68), a clinician can extend a first tissue piercing wire (70) across the tissue at the first treatment location (68) as illustrated in FIG. 5. The first tissue piercing wire (70) is introduced through central lumen (66) of the first wire delivery catheter (60). The first tissue piercing wire (70) tracks through the axial lumen (66) of the first wire delivery catheter (60), extends distally from its proximal end, contacts the first treatment location (68), further extends distally, with its distal end (72) crosses the tissue at the first treatment location (68) from one side to another side.

In some embodiments, not specifically shown in FIG. 5, at the first treatment location, the distal end (72) of the first tissue piercing wire (70) extends across the tissue of the first papillary muscle (26a) alone, across the tissue of the ventricle walls, including within or through features created by trabeculae carneae (32) alone, or across the tissue of the trabeculae carneae (32) and papillary muscle (26a) together. In an alternative embodiment, at the first treatment location, the distal end (72) of the first tissue piercing wire (70) extends under the bridge (34) formed by the trabeculae carneae (32) and across the tissue of the trabeculae carneae (32) and/or papillary muscle (26a). One skilled in the art should understand that human anatomy varies from individual to individual. Thus, embodiments disclosed herein should not be viewed as limiting to the scope of the present teachings.

According to some embodiments, the tissue piercing wire has a piercing tip which allows it to perforate the heart tissue/muscle. According to other embodiments, the tissue piercing wire has a radio frequency (RF) energy delivery tip to assist its crossing of the heart tissue/muscle. In these other embodiments, a suitable RF energy generating device (not shown) is coupled to the wire.

Yet according to other embodiments, the first wire delivery catheter also includes an extendable needle at its distal end that is capable of piercing the heart tissue/muscle. The tissue piercing wire tracks through the lumen of such wire delivery catheter, extends through the aperture created by the extendable needle of the first wire delivery catheter, reaches the opposite side of the tissue at the first treatment location. One skilled in the art would understand that other methods and devices can also be used to cross a wire through the heart tissue/muscle. Thus, the particular examples described herein should be not viewed as limiting to the scope of the present teachings.

According to some embodiments, the distal portion of the tissue piercing wire is designed to deflect or curl back to prevent inadvertent tissue damage. The ability to deflect or curl can be achieved by the geometrical construct of the tissue piercing wire, such as a flexible distal portion, by the physical property of the material used in making the tissue piercing wire, or by the shape memory property of the material used in making the tissue piercing wire. Those skilled in the art would be able to incorporate known techniques and/or material to achieve this purpose without undue experimentation.

Figure 6:
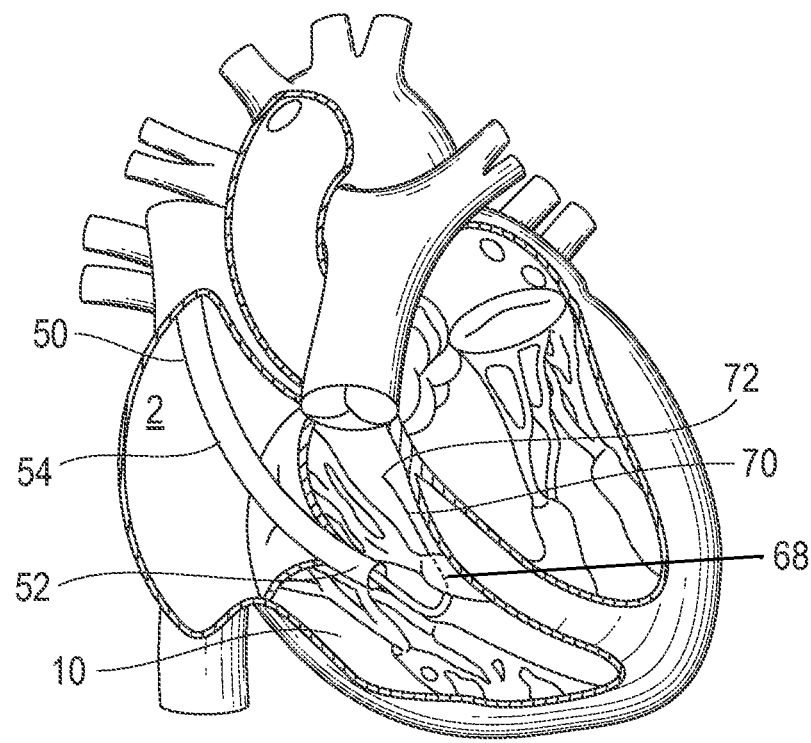
FIG. 6 is a perspective view of an exemplary tissue piercing wire across the tissue at a treatment location in accordance with the present teachings.
Figure 8A:
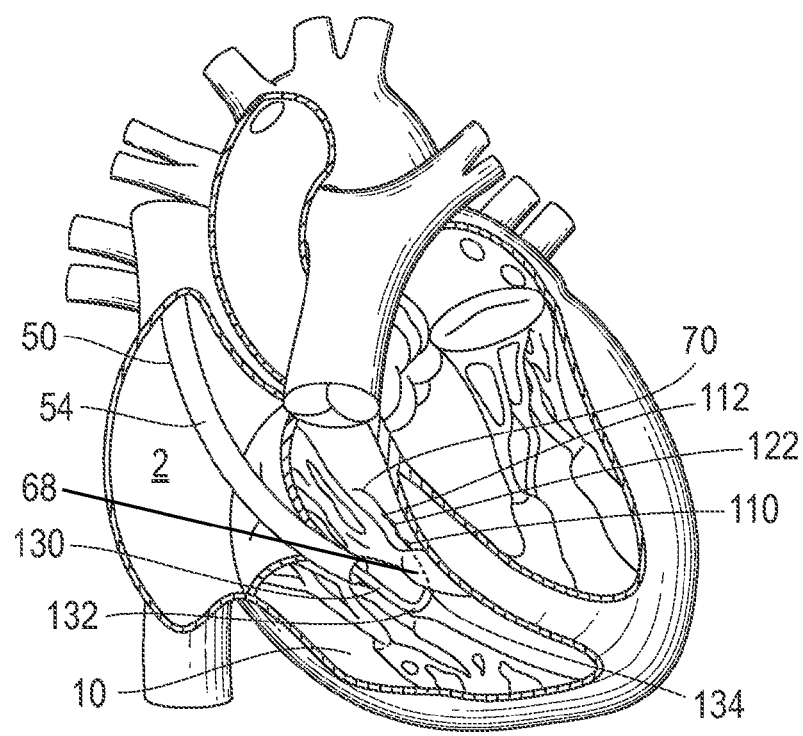
FIGS. 8a-8c are perspective views of an exemplary tissue anchor deploying at a treatment location in accordance with the present teachings.
Figure 8B:
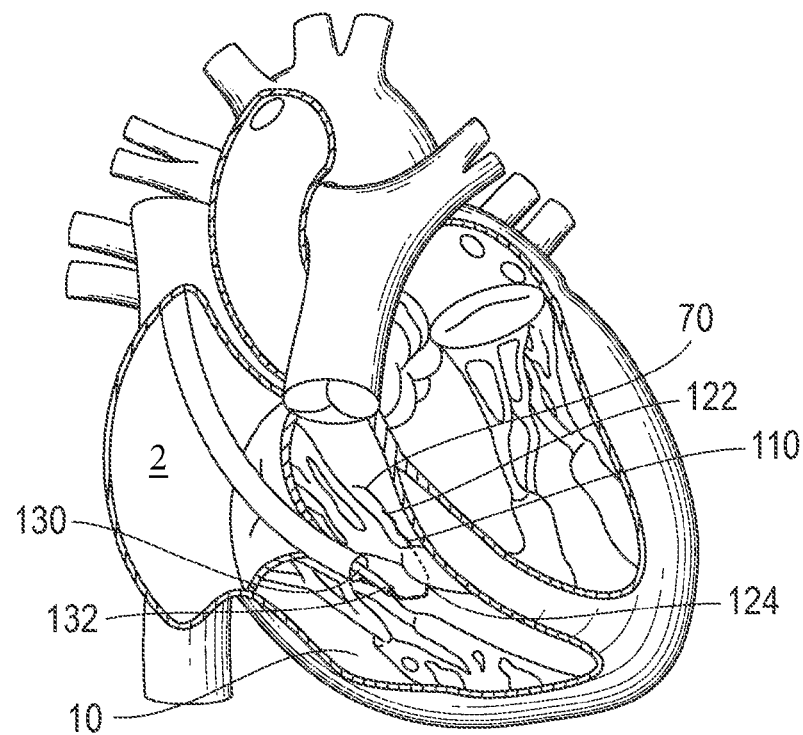
Figure 8C:
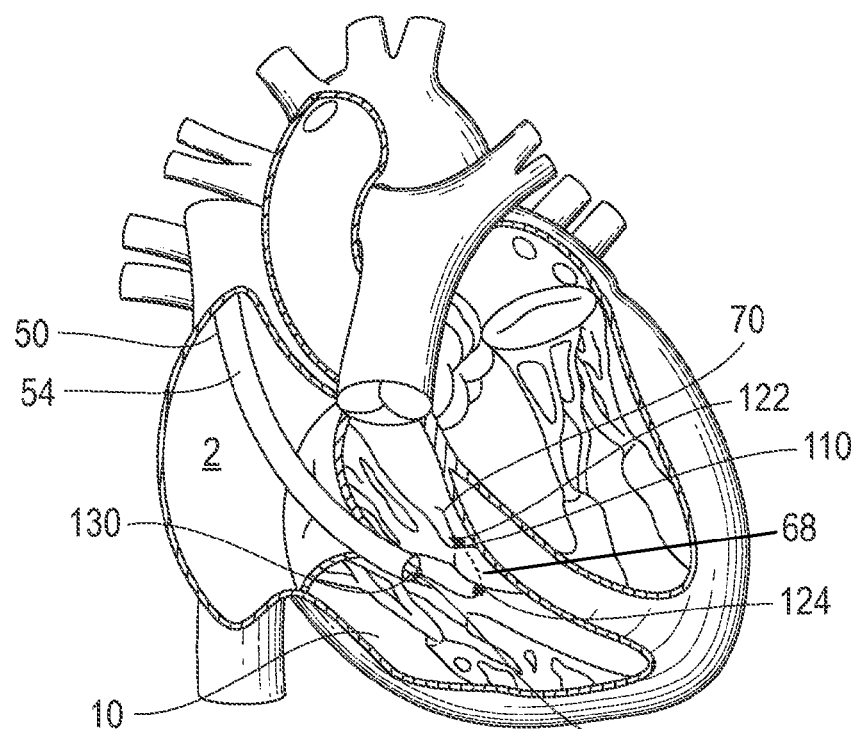

With the first tissue piercing wire (70) in place across the tissue at the first treatment location (68), in various embodiments, the first wire delivery catheter (60) is removed as illustrated in FIG. 6. Then, a first tissue anchor (110) is then deployed. According to some embodiments, as illustrated in FIGS. 8a-c, a first tissue anchor delivery catheter (130) tracks along the first tissue piercing wire (70), across the tissue at the first treatment location (68) and delivers the first tissue anchor (110).

Figure 38:
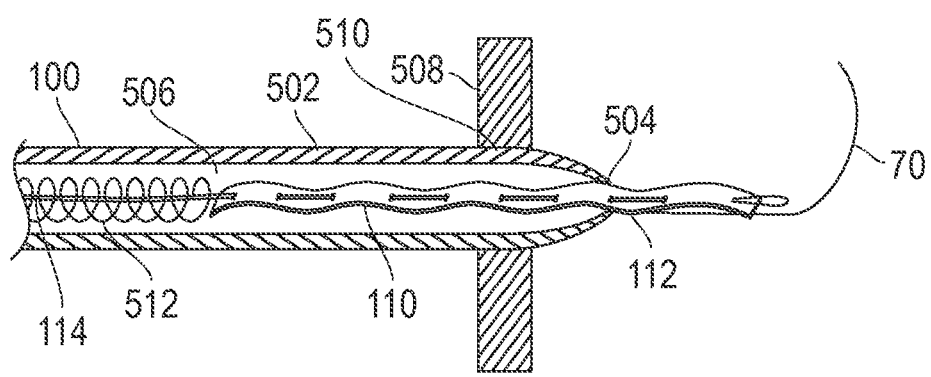
FIG. 38 is a perspective view of an exemplary tissue anchor delivery catheter in accordance with the present teachings.

According to some embodiments of the present teachings, as illustrated in FIG. 38, a tissue anchor delivery catheter (100) has a proximal end (not shown), a distal portion (502) with a distal end (504), and a central lumen (506) extending in between. The tissue anchor delivery catheter (100) is configured to rides over the first tissue piercing wire (70), where the first tissue piercing wire (70) extends along inside the central lumen (506) of the tissue anchor delivery catheter (100).

According to one embodiment of the present teachings, the distal portion (502) (of the tissue anchor delivery catheter (100) is configured to expand the hole (510) in the tissue (508) created by the tissue piercing wire (70). As such, the outer profile of the distal portion (502) of the tissue anchor delivery catheter (100) has a small distal end (504), which then gradually enlarges, as illustrated in FIG. 38. In one exemplary embodiment of the present teachings, as illustrated in FIG. 38, the wall thickness and the inner diameter of the distal end (504) of the first tissue anchor delivery catheter (100) is small. The wall thickness and the inner diameter of the distal portion (502) of the tissue anchor delivery catheter (100) then gradually expand. This gradual expansion allows the distal portion (502) of the tissue anchor delivery catheter (100) to cross through the tissue (508) at the first treatment location with relative ease.

Further referring to FIG. 38, the distal portion (502) of the tissue anchor delivery catheter (100) is configured to allow for a tissue anchor (110) to be delivered through its distal end (504). For example, the tissue anchor (110) is pushed out of the distal end (504) of the tissue anchor delivery catheter (100) by a suitable pushing element (512) that slidably disposed within the tissue anchor delivery catheter (100), for example, a simple stainless steel coil. In some embodiments, as illustrated in FIG. 38, the stainless steel pushing coil could have an internal diameter large enough to accommodate the tensioning member (114) extending from the tissue anchor (110). One skilled in the art should understand that other design and configuration of the tissue anchor delivery catheter (100) could also be used to achieve the purpose of the delivery a tissue anchor (110). For example, instead of exiting the distal end (504) of the tissue anchor delivery catheter (100), a tissue anchor (110) can be pushed distally out of a side hole near the distal end (504) of the tissue anchor delivery catheter (100). In another example, the tissue anchor (110) could be pushed through a perforated or slotted section of at or near the distal end (504) of the tissue anchor delivery catheter (100). Thus, the specific exemplary embodiment described above should be not viewed as limiting to the scope of the present teachings.

Figure 7:
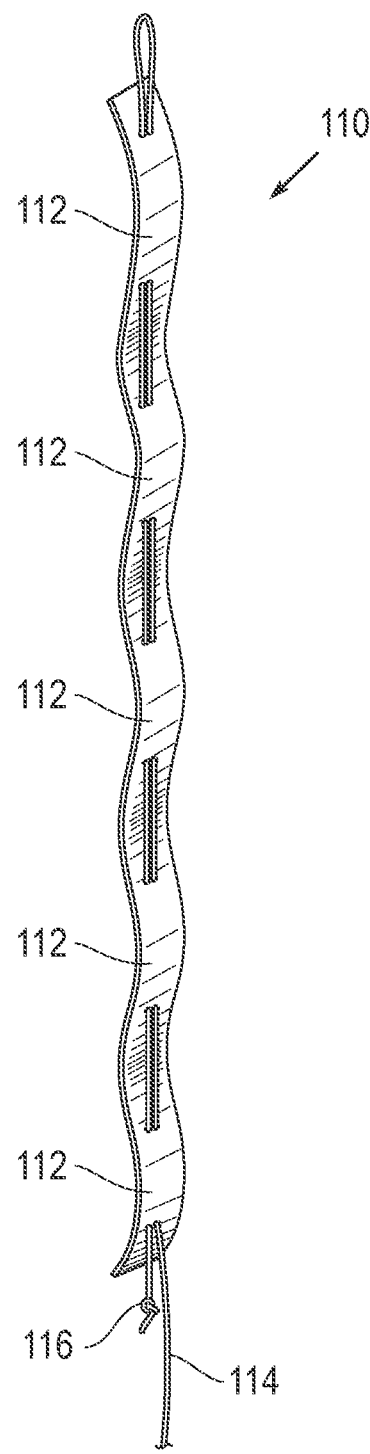
FIG. 7 is a perspective view of an exemplary tissue anchor in accordance with the present teachings.

While any tissue anchoring devices known in the art can be used, the particular tissue anchor in the present teachings is collapsible. In various embodiments, as illustrated in FIG. 7, a tissue anchor (110) comprises a plurality of discrete, flat, or flexible anchor elements (112) coupled with a flexible tension member (114). The anchor elements (112) can be made from a surgical grade fabric material (e.g., a polyester material such as DACRON), in some instances, designed to promote tissue in-growth so that the anchors become at least in part encased in tissue over-time. The anchor elements (112) are coupled to a tension member (114), in this example, a suture, by threading the suture distally through the anchor elements (112) and proximally through the anchor elements (112). A slip knot (116) or another type of locking mechanism is formed so that when a proximal end (not shown) of the tension member (114) is pulled, the anchor elements (112) will be drawn together. This leaves a long "tail" of the suture leading from the anchor (110) to the venous access site, and the long "tail" can be used for subsequent tensioning, as described herein.

Examples of a tissue anchor and a tissue anchor delivery catheter described in conjunction with the drawings of the present teachings have some similarities to those in U.S. patent application Ser. No. 12/273,670, filed on Nov. 19, 2008, entitled Tissue Anchor and Anchoring System, U.S. patent application Ser. No. 11/174,951, filed on Jul. 5, 2005, entitled Tissue Anchor, Anchoring System and Methods of Using the Same, U.S. patent application Ser. No. 13/777,042, filed on Feb. 26, 2013, entitled Tissue Anchor and Anchoring System, each of which is incorporated by reference herein in its entirety. Though not shown in the exemplary figures, other suitable tissue anchors can also be used. Examples of suitable tissue anchors include, but are not limited to, tissue fasteners, tissue pledgets, automatically expanding metallic scaffolds, or tissue staples etc.

FIGS. 8a-8c illustrate an exemplary delivery and deployment of a first tissue anchor (110) across the tissue at the first treatment location (68). FIG. 8a illustrates the process of exposing of the distal portion (122) of the first tissue anchor (110), and FIG. 8b illustrates the process of exposing the proximal portion (124) of the first tissue anchor (110), where the first tissue anchor (110) tracks along the tissue piercing wire (70) at the location according to the embodiments depicted in FIGS. 3 and 5. FIG. 8c illustrates an exemplary deployment of the first tissue anchor (110) at the first treatment location (68).

Referring to FIG. 8a, a first tissue anchor delivery catheter (130) holding a first tissue anchor (110) inside its longitudinal lumen (132) tracks along a tissue piercing wire (70), across the tissue at the first treatment location (68). Continuing referring to FIG. 8a, the first tissue anchor (110) is partially pushed distally outside of the distal end (134) of the first tissue anchor delivery catheter (130). Once the distal portion (122) of the first tissue anchor (110) or a sufficient amount of the anchor elements (112) is exposed at the distal side across the tissue at the first treatment location (68), a clinician stops pushing the first tissue anchor (110) distally and retracts the first tissue anchor delivery catheter (130) proximally. Retracting the first tissue anchor delivery catheter (130) proximally exposes the proximal portion of the first tissue anchor (110) which is roughly on the opposite side of tissue at the first treatment location (68) from the distal end of the first tissue anchor. The first tissue anchor (110) therefore spans from distal side of the treatment site, through the tissue of the first treatment location (68), and to the proximal side of the treatment site. As illustrated in FIG. 8c, to deploy the first tissue anchor (110), the clinician pulls the proximal end (118) of the tension member (114) such that the anchor elements (112) of the first tissue anchor (110) are drawn together against the opposite sides of the tissue at the first treatment location (68), thereby securing the first tissue anchor (110) to tissue at the first treatment location (68). As a result, as illustrated in FIG. 8*c*, the first tissue anchor (110) is deployed across the tissue at the first treatment location (68) with the distal portion (122) of the first tissue anchor (110) placed against the distal side of the tissue, the proximal portion (124) of the first tissue anchor (110) placed against the proximal side of the tissue, and the tension member (114) of the first tissue anchor (110) extending proximally through the lumen (132) of the first tissue anchor delivery catheter (130) to the outside of the body. According to some embodiments, the tissue piercing wire (70) that marks tissue access during the deployment of the first tissue anchor (110) is then withdrawn proximally outside of the body, while the proximal end of the tension member (114) is controlled by the clinician from outside of the body.

Figure 9:
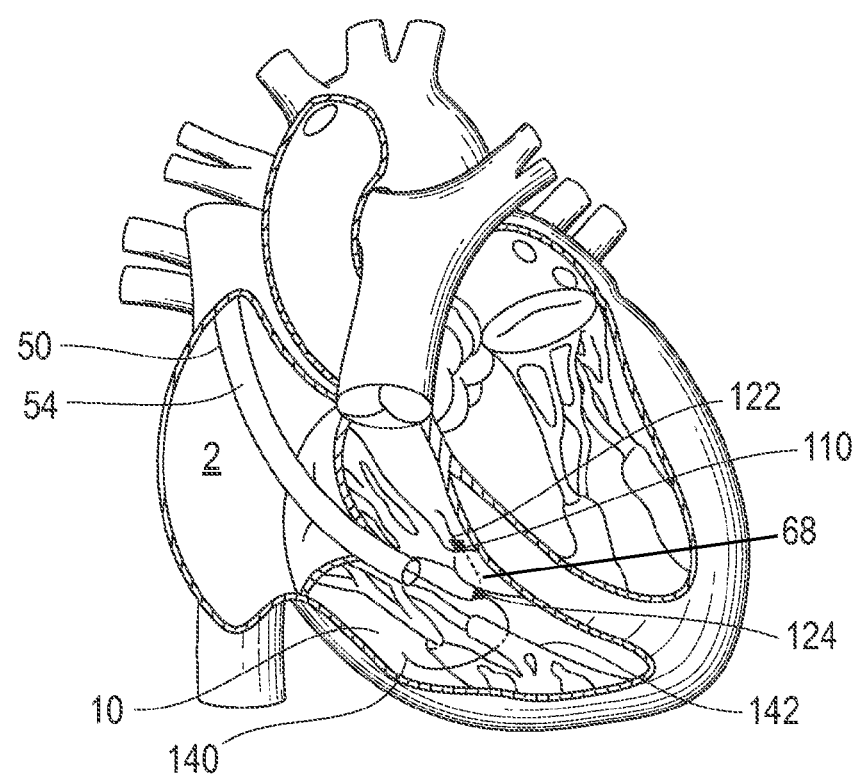
FIG. 9 is a perspective view of an exemplary tissue piercing wire across the tissue at a second treatment location in accordance with the present teachings.

With the first tissue anchor (110) deployed across the tissue at the first treatment location (68), the clinician can then deploy a second tissue anchor across the tissue at the second treatment location. According to some embodiments, similar to what is described in accordance with FIGS. 3-8, a clinician uses similar steps to position a second wire delivery catheter against the tissue at the second treatment location inside the right ventricle (10). According to some embodiments, the positioning of the second wire delivery catheter against the proximal side of the tissue at the second treatment location includes extending, retracting, turning, pivoting, or otherwise manipulating the second wire delivery catheter to the tissue at the second treatment location, similar to the methods described herein or known to those with ordinary skill in the art. Then a second tissue piercing wire is advanced through the lumen of the second wire delivery catheter with its distal end across the tissue at the second treatment location. FIG. 9 illustrates a second tissue piercing wire (140) placed at the second treatment location (142).

Figure 10:
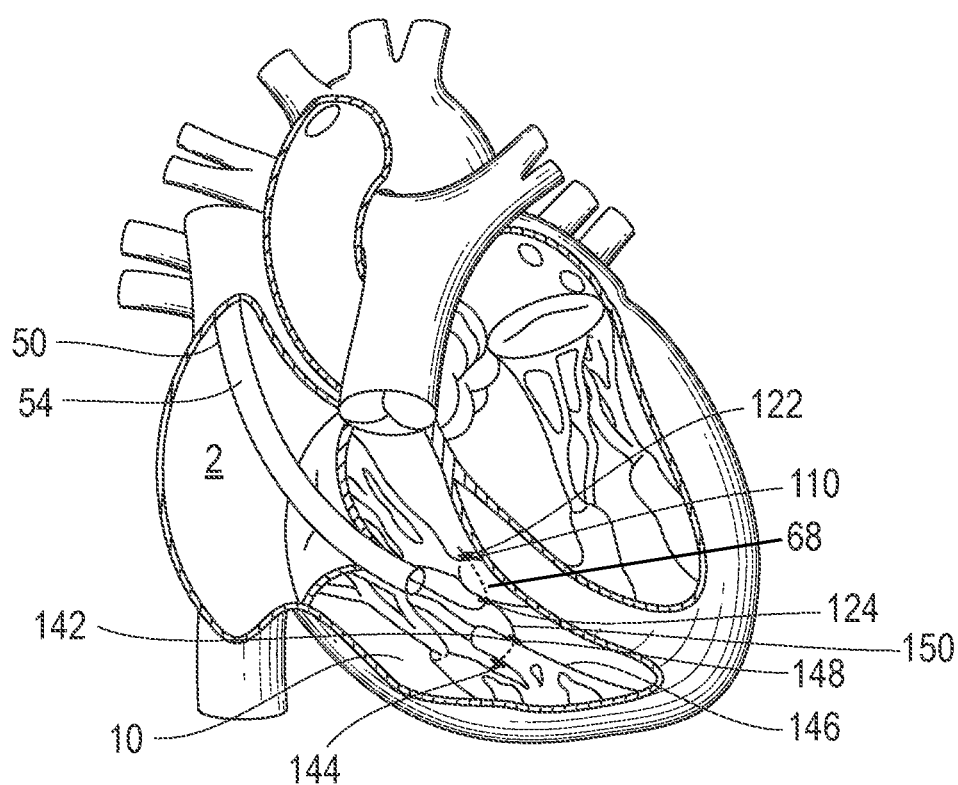
FIG. 10 is a perspective view of an exemplary tissue anchor deployed at a second treatment location in accordance with the present teachings.

In various embodiments, a second tissue anchor (144) is deployed at the second treatment location (142) across the tissue according to various embodiments described herein in accordance with FIGS. 8*a-c*. FIG. 10 illustrates that the second tissue anchor (144) is deployed across the tissue at the second treatment location (142) with the distal portion (146) of the second tissue anchor (144) placed against the distal side of the tissue, the proximal portion (148) of the second tissue anchor (144) placed against the proximal side of the tissue, and the tension member (150) of the second tissue anchor (144) extending proximally through the venous access to the outside of the body. At this point, the second tissue piercing wire (140) can be removed.

According to one embodiment, the second treatment location is at or near the base of a second papillary muscle, such as the posterior or anterior papillary muscle. Alternatively, the second treatment location is at or near the middle portion of a second papillary muscle, such as the posterior or anterior papillary muscle. In some embodiments, the second treatment location is near the trabeculae carneae at the base of the second papillary muscle. One skilled in the art would understand that other locations along with the second papillary muscle can also be used as a second treatment location.

Figure 11:
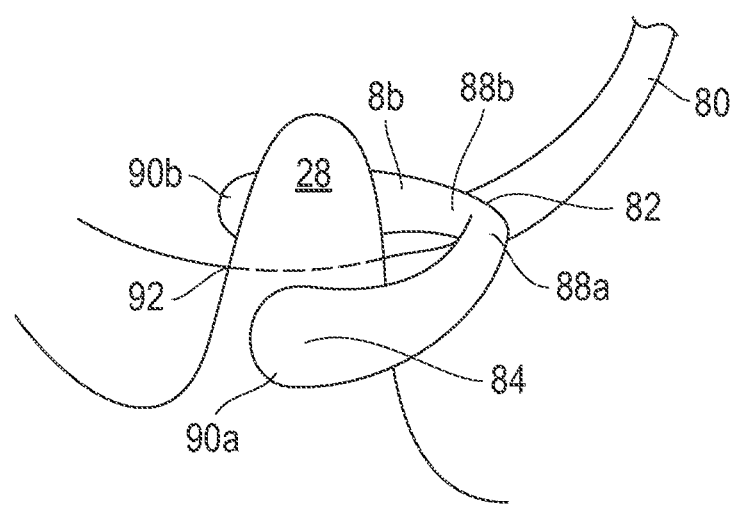
FIG. 11 is a perspective view of another exemplary wire delivery catheter in accordance with the present teachings.
Figure 12:
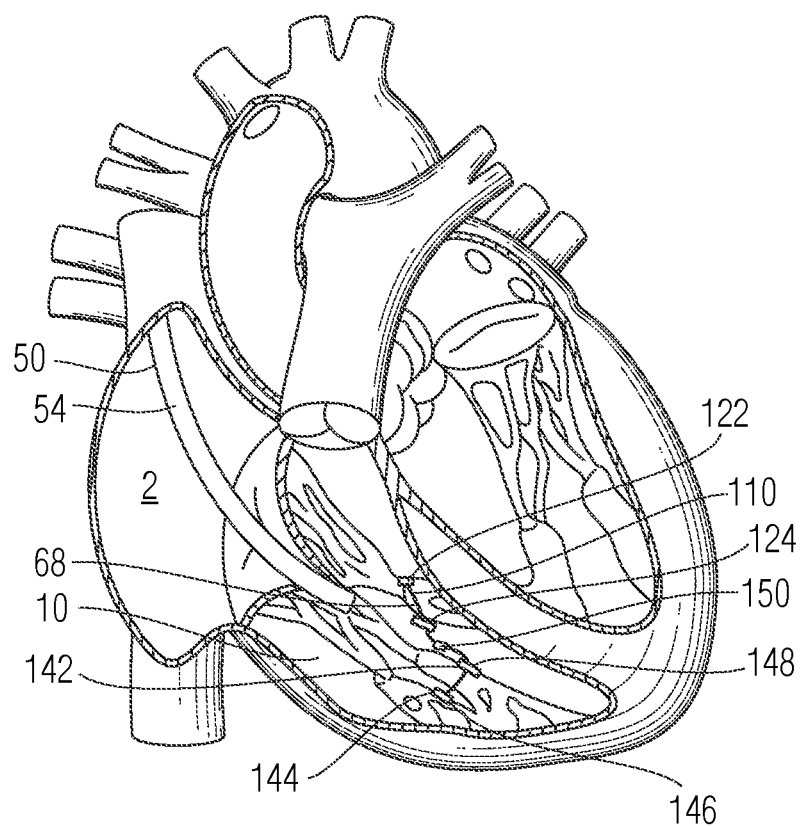
FIG. 12 is a perspective view of an exemplary suture lock tensioning two exemplary tissue anchors toward each other in accordance with the present teachings.

FIG. 11 illustrates an alternative embodiment of the wire delivery catheter (80), where the distal end (82) of the wire delivery catheter (80) has two separating halves (84, 86), adapted to be positioned against the opposite side of the papillary muscle (28) before the tissue piercing wire (92) piercing across the tissue. As seen in FIG. 11, each of the separating halves (84, 86) has a fixed end (88*a-b*), and a free end (90*a-b*).

In one embodiment, the two separating halves (84, 86) are integral part of the distal end (82) of the wire delivery catheter (80). In another embodiment, the two separating halves (84, 86) are separated pieces that attach to the distal end (82) of the wire delivery catheter (80).

In some embodiments, the two separating halves (84, 86) have a delivery configuration where the two halves (84, 86) are pivoted radially inward in order to achieve a smaller radial profile, as illustrated in FIG. 11. In other embodiments, the two separating halves (84, 86) have a deployed configuration where the two halves are pivoted radially outward so that the halves (84, 86) are positioned directly against the opposing side of the papillary muscle (28), as shown in FIG. 11. In some embodiments, the radial pivoting is achieved by a pre-formed configuration, where the two separating halves (84, 86) are pre-formed to be radially outward from the longitudinal axis of the first wire delivery catheter (60). During delivery, the two separating halves (84, 86) are constrained by a separate catheter/sheath, such as the guide (50). Once freed from the constraint, the two separating halves (84, 86) resume their pre-formed radially outward configuration. In alternative embodiments, the radial pivoting of the two separating halves (84, 86) is achieved by an actuation mechanism controlled by a clinician from outside of the body. That is, during a delivery, the two separating halves (84, 86) are placed in its radially inward configuration, and once inside the right ventricle (10) and near the treatment location, the clinician actuates the two separating halves (84, 86), so that they pivot radially outward.

In some embodiments, during the positioning of the wire delivery catheter (60), a clinician deploys the two separating halves (84, 86) inside the right ventricle (10), then slides the two separating halves (84, 86) toward and around the papillary muscle. Accordingly, the first papillary muscle (28) is situated in between the two separating halves (84, 86) as shown in FIG. 11. In some embodiments, the space between the two deployed separating halves (84, 86) is about or slightly larger than the size of the papillary muscle. In another embodiment, the space between the two deployed separating halves (84, 86) is significantly larger than the size of the papillary muscle.

In some embodiments, upon positioning the papillary muscle (28) within the space between the two deployed separating halves (84, 86), the space between the two separating halves (84, 86) are then reduced to secure the papillary muscle (28) inside. Such reduction in space is achieved either by partially constraining the two separating haves (84, 86) with the distal end portion of a catheter/sheath or the guide (50), or by a mechanical actuation controlled by a clinician from outside of the body, thereby allowing the two separating halves (84, 86) pivot inward and secure the papillary muscle (28).

In one embodiments, each, or all, of the separating halves (84, 86) has a profile in the shape of a spoon, a flat finger, a half pipe, and etc. In some embodiments, each, or all, of the separating halves (84, 86) could have a relatively straight profile. In an alternative embodiment, each, or all, of the separating halves (84, 86) could have a curved profile, which each half curves toward the other one. In some embodiments, each, or all, of the separating halves (84, 86) has an enlarged free end, and a relative small fixed end. In an alternative embodiments, each, or all, of the separating halves (84, 86), has a generally uniform cross-sectional profile from its fixed end to its free end. In some embodiments the two separating halves (84, 86) of the wire delivery catheter (80) of are constructed of simple loops of wire. For example, the two separating sections (84, 86) of the wire delivery catheter (80) may be made of a pre-formed loop of Nitinol wire which is formed into a sort of a butterfly wing shape. As another example, the two separating halves (84, 86) of the wire delivery catheter (80) may be made of a pre-formed stainless steel.

In other embodiments the two separating halves may slidably reside inside the sheath of the wire delivery catheter. Such two halves could therefore be positioned in a collapsed configuration inside the wire delivery catheter until the wire delivery catheter is near the papillary muscles. At this point the two separating halves could be pushed distally by the clinician and the two halves, upon exiting the distal end of the sheath of the wire delivery catheter, would automatically separate and cradle the papillary muscle as depicted in FIG. 11.

In some embodiments the two separating halves are configured to wrap partially or completely around the papillary muscle, thereby temporarily securing the wire delivery catheter to the base of the papillary muscle. One skilled in the art should understand that the two separating halves could have any shapes, sizes, configurations, so long as the intended function is satisfied. Thus, the specific embodiments disclosed here should not be construed as limiting.

FIG. 12 illustrates an exemplary embodiment of reshaping and resizing the right ventricle (10) by drawing two tissue anchors toward each other. According to some embodiments, a clinician applies tension to one or both of the tension members of the tissue anchors. This tension pulls two tissue anchors closer to each other, thereby reducing the distance between the two treatment locations. This tension and the reduced distance between the two tissue anchors are then kept by mechanisms known to those in the field, for example, by directing a suture lock (150) along the tension members towards the tissue anchors. Suitable suture locks include those well known in the art and those described in U.S. application Ser. No. 11/753,921, filed on May 25, 2007, entitled Suture locks for Surgical Tension members and Methods of Using the Same to Secure Surgical Tension members, the disclosure of which is incorporated herein by reference. While the tension members are secured by the suture lock (150), the excess tension members, i.e. the tension member at the proximal side of the suture lock (150) can be removed by a cutter, for example, a cutter disclosed in U.S. patent application Ser. No. 11/935,054, filed on Nov. 5, 2007, entitled Suture Cutter and Method of Cutting Suture, the disclosure of which is incorporated herein by reference. The guide (50) along with all the first and/or second wire delivery catheters and/or the first and/or second tissue anchor delivery catheters, and/or the suture lock delivery catheters can then be retracted proximally and removed from the body.

According to one embodiment, the suture lock (150) is positioned close to the first treatment location (68). In another embodiment, the suture lock (150) is positioned close to the second treatment location (142). In an alternative embodiment, the suture lock (150) is positioned somewhere between the first and second treatment locations (68, 142).

Figure 13:
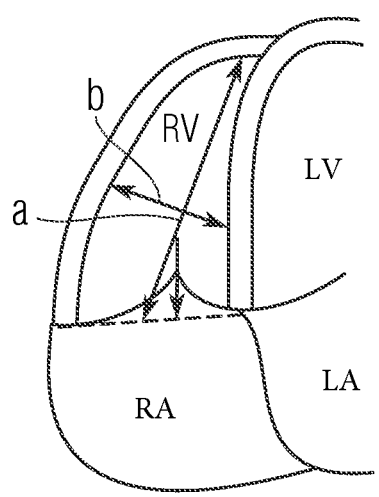
FIG. 13 is illustrates the right ventricle sphericity index, and a measurement of a tricuspid valve tethering height.

Upon reducing the distance between the two treatment locations, the right ventricle (10) is reshaped and resized. In one embodiment the reduction in the distance between the two treatment locations is configured such that the geometric changes in the right ventricle and subvalvular apparatus results in a significant decrease in the presence or amount of regurgitation through the tricuspid valve. In some embodiments the reduction in the distance between the two treatment locations is configured such that there is a predetermined change in the geometry in the tricuspid valve annulus. For example, the tension members may be tensioned until the septal-lateral dimension of the tricuspid valve is reduced by 3-6 mm. In one embodiment, the reduction in distance between the two treatment locations is configured so that the reduction in the right ventricle sphericity index, which is calculated as a ratio of the right ventricular short-axis line to the right ventricular long-axis line, as illustrated in FIG. 13, is within 25-40%. The right ventricular long-axis line is the line from the true right ventricular apex to the midpoint of the tricuspid annulus line. The right ventricular short-axis line is the line between the right ventricular wall and the septum perpendicular to the right ventricular long-axis line at its midpoint. In another embodiment, the reduction in distance between the two treatment locations is configured so that the tricuspid valve tethering height is reduced by 4-10 mm. The tricuspid valve tethering height is the largest height between the tricuspid annulus (24) line and the coapting point between the tricuspid valve leaflets, as illustrated in FIG. 13. In another embodiment, the reduction in distance between the two treatment locations is configured to be roughly 30-50% of the initial distance between the two treatment locations In one embodiment, the first and second treatment locations are at the middle or the base of the anterior and posterior papillary muscles. In another embodiment, the first and second treatment locations are at the middle or the base of the anterior and septal papillary muscle. In yet another embodiment, the first and second treatment locations are at the middle or the base of the posterior and septal papillary muscle.

Figure 14A:
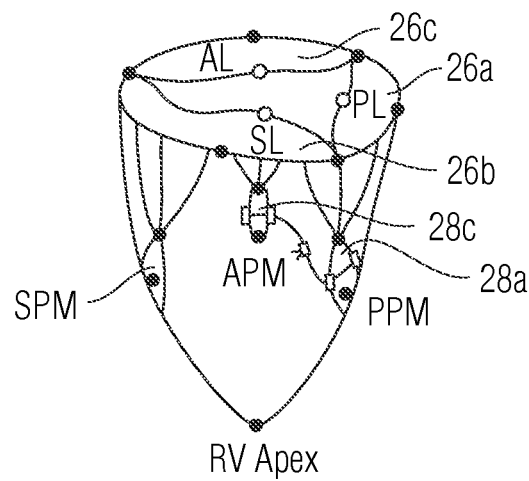
FIGS. 14a-14c are perspective views of an exemplary tissue anchor-tension member-lock system deployed inside the right ventricle in accordance with the present teachings.
Figure 14B:
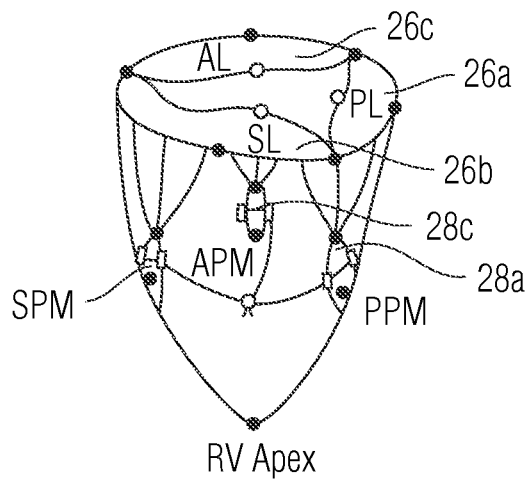
Figure 14C:
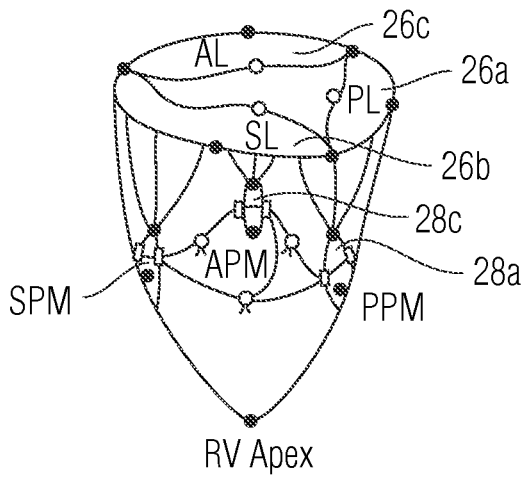

In one embodiment, two papillary muscles are secured and tensioned together by the above described tissue anchor-tension member-lock system as illustrated in FIG. 14a. In another embodiment, the three papillary muscles are secured and tensioned together by the above described tissue anchor-tension member-lock system as illustrated in FIG. 14b. In yet another embodiment, a first papillary muscle is secured and tensioned to a second papillary muscle by the above described tissue anchor-sutures-suture lock system, and the second papillary muscle is secured and tensioned to the third papillary muscle by the above described tissue anchor-sutures-suture lock system, as illustrated in FIG. 14c.

Figure 15:
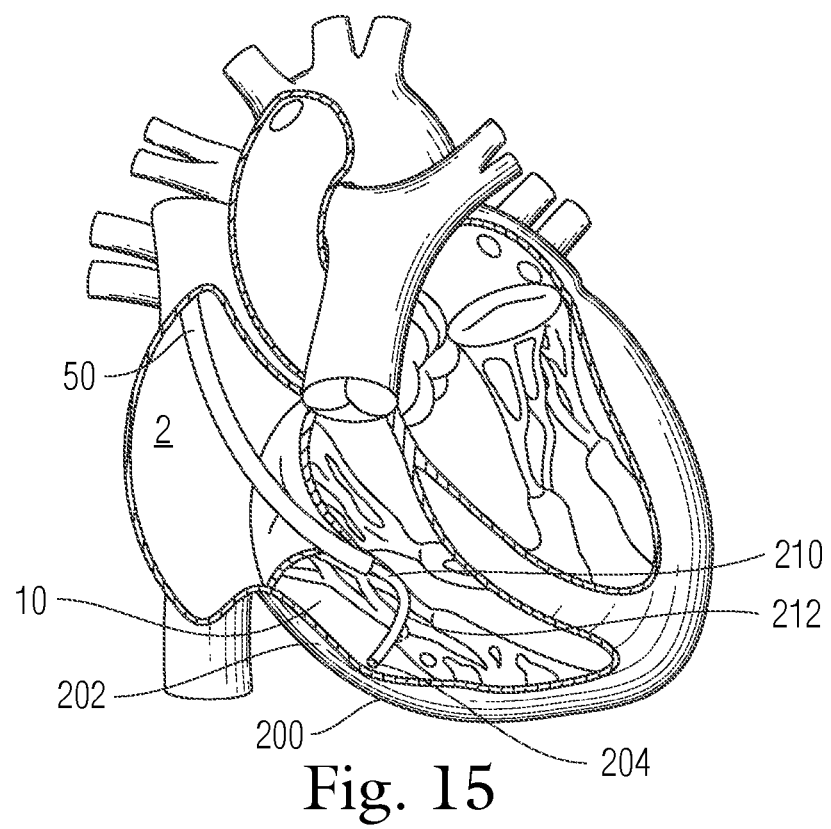
FIG. 15 is a perspective view of another exemplary wire delivery catheter directed into the right ventricle in accordance with the present teachings.

One skilled in the art would understand that embodiments described above could also be used to reshape and resize the right ventricle (10) by pulling the right ventricle wall (200) inward. FIGS. 15-20 illustrate other embodiments of the present teachings where the right ventricle wall (200) is tensioned inward at three locations by tension members. FIG. 15 illustrates a wire delivery catheter (210) with a bend distal end portion (212), for example similar to the embodiments described above, specifically with reference to FIGS. 3-4, is extended, retracted, turned, or otherwise toward the first treatment location (202) on the right ventricle wall (200), with its distal end (204) directly opposed against a first treatment location (202) on the right ventricle wall (200).

Figure 16:
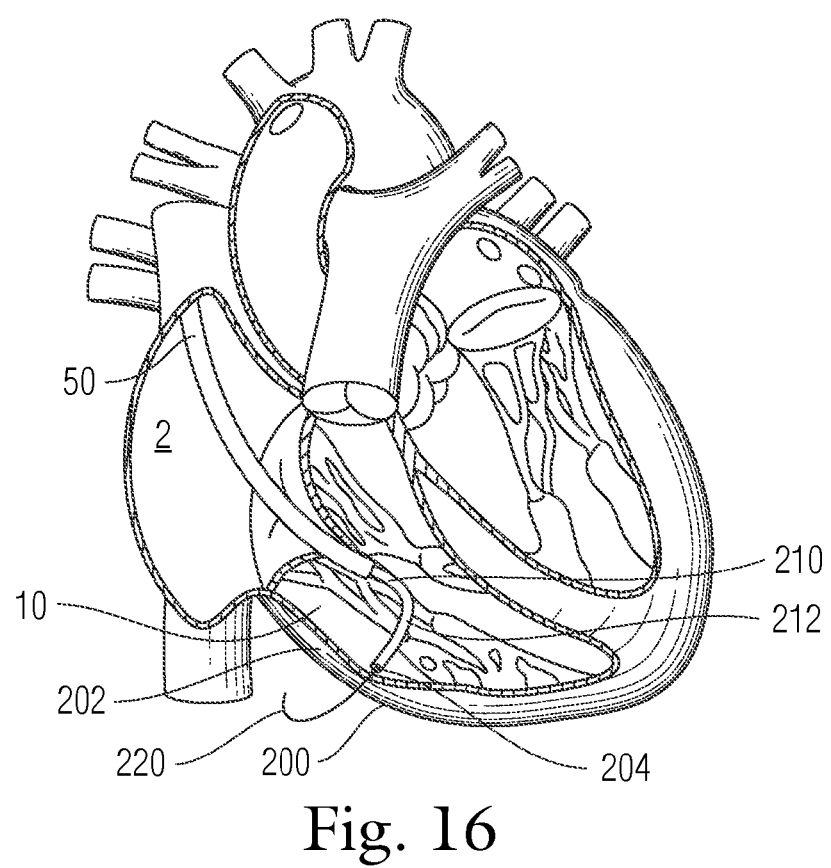
FIG. 16 is a perspective view of another exemplary wire delivery catheter delivering another exemplary tissue piercing wire across the tissue at a treatment location in accordance with the present teachings.
Figure 17:
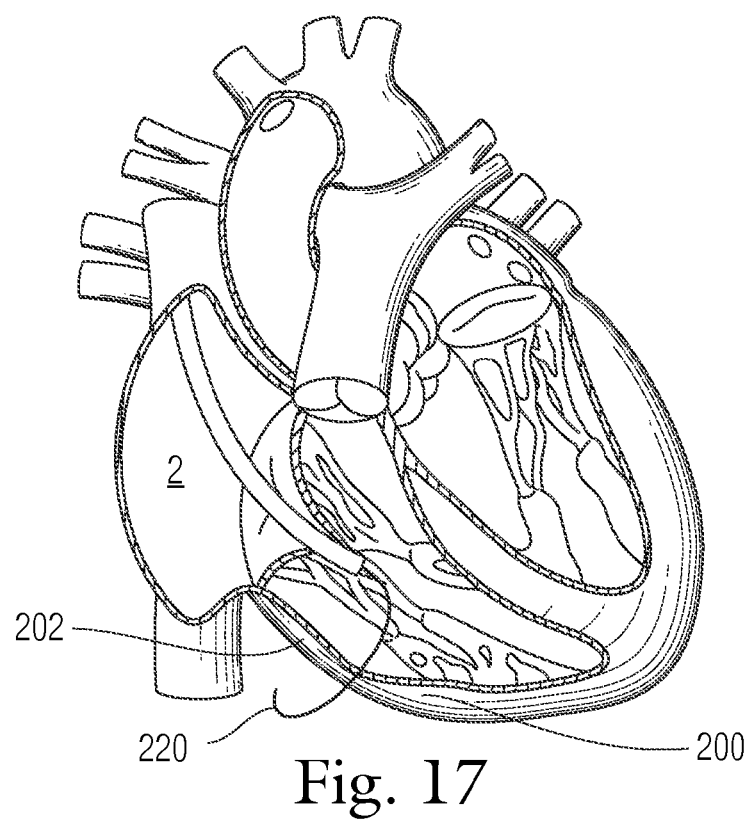
FIG. 17 is a perspective view of another exemplary tissue piercing wire across the tissue at a treatment location in accordance with the present teachings.
Figure 18:
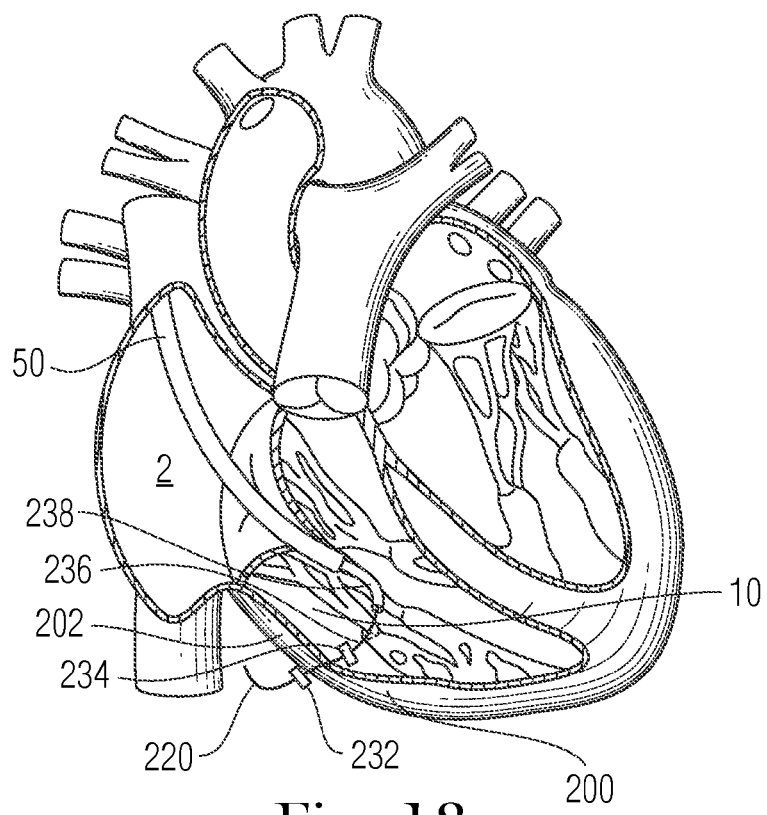
FIG. 18 is a perspective view of another exemplary tissue anchor deployed at a treatment location in accordance with the present teachings.

FIG. 16 illustrates a tissue piercing wire (220) piercing the right ventricle wall (200), in a manner similar with those described above, for example with reference to FIG. 5. After removing the first wire delivery catheter (60), the tissue piercing wire (220) keeps the first treatment location on the right ventricle wall as illustrated in FIG. 17. A first tissue anchor delivery catheter tracks along the wire, reaches the first treatment location (202) across the ventricle free wall. Similar to what has been described above, for example with reference to FIGS. 7 and 8a-8c, the distal portion (232) of the first tissue anchor (230) is deployed against the distal side of the ventricle wall (200), outside the heart; and the proximal portion (234) of the first tissue anchor (230) is deployed against the proximal side of the ventricle wall (200), inside the heart; and the tension member (236) of the first tissue anchor (230) extending proximally through the lumen of the tissue anchor delivery catheter (238) to the outside of the body, as illustrated in FIG. 18. According to some embodiments, the tissue piercing wire (202) that marks first tissue anchor implantation location is then withdrawn proximally outside of the body, while the proximal end of the tension member (236) is controlled by a doctor from outside of the body.

Figure 19:
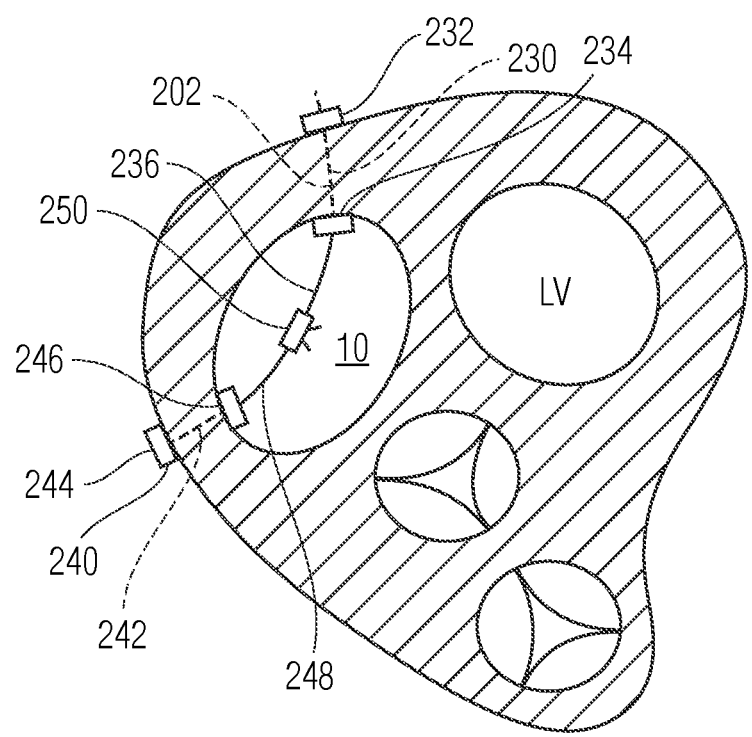
FIGS. 19, 20a and 20b are perspective views of another exemplary tissue anchor-tension member-lock system deployed inside the right ventricle in accordance with the present teachings.

With the first tissue anchor (230) deployed across the first treatment location (202) on the right ventricle wall (200), the clinician can then deploy a second tissue anchor (240) at a second treatment location (242) on the right ventricle wall (200). According to some embodiments, similar to what is described related to FIGS. 9-10, a clinician uses similar steps to position a wire delivery catheter against the second treatment location (242) on the right ventricle wall (200), extend a second wire across the heart wall, and deploy a second tissue anchor (240) at the second treatment location (242), so that the distal portion (244) of the second tissue anchor (240) is deployed against the distal side of the ventricle wall (200), outside the heart; the proximal portion (246) of the second tissue anchor (240) is deployed against the proximal side of the ventricle wall (200), inside the heart; and the tension member (248) of the second tissue anchor (240) extending proximally to the outside of the body. Similar to what has been described above, for example, with reference to FIG. 12, according to some embodiments, a clinician applies tension to one or both of the tension members (236, 248) of the tissue anchors (230, 240). This tension pulls two tissue anchors (230, 240) closer to each other, thereby reducing the distance between the two treatment locations (202, 242). This tension, and the reduced distance between the two tissue anchors (230, 240), are then kept by a suture lock (250) along the tension members (236, 248) towards the tissue anchors (230, 240), as illustrated in FIG. 19.

Similar to what has been described above, according to one embodiment, the suture lock (250) is positioned close to the first treatment location (202). In another embodiment, the suture lock (250) is positioned close to the second treatment location (242). In an alternative embodiment, the suture lock (250) is positioned somewhere between the first and second treatment locations (202, 242).

Figure 20A:
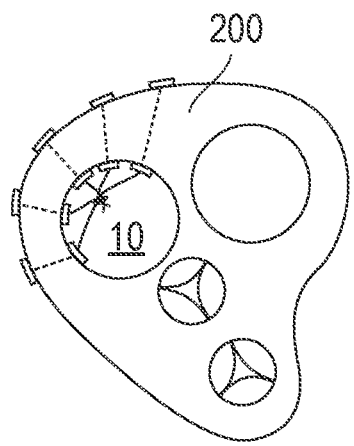
Figure 20B:
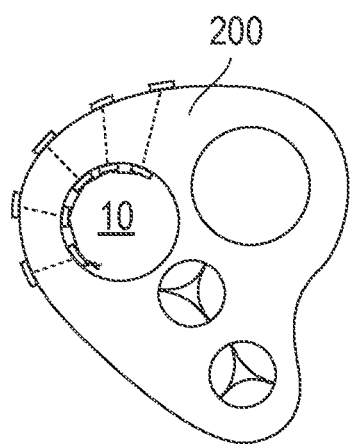

Although FIGS. 15-19 illustrate two locations on the ventricular wall are tensioned by the tissue anchor-sutures-suture lock system, one with ordinary skill in the art should understand that more than two locations on the ventricular free wall could be secured and tensioned together by the above described tissue anchor-sutures-suture lock system. A clinician can optionally deploy a third tissue anchor at a third treatment location on the right ventricle wall (200) using similar steps described. One skilled in the art should appreciate that more than three tissue anchors can also be deployed along the right ventricle wall (200), and all tissue anchors could be tensioned together by one suture lock (250), for example as illustrated in FIG. 20a. Alternatively, each neighboring two tissue anchors are tensioned together by one suture lock. In another embodiment, as illustrated in FIG. 20b, all tissue anchors slide over one suture, and upon deployment, one suture lock maintains the tension the clinician applied on the suture. One skilled in the art should understand that the specific shape and design of the tissue anchor, the specific number and implantation locations of the tissue anchors, as well as the manner suture lock is incorporated to keep the tension applied on the suture disclosed herein is only examples for the purpose to illustrate present teachings. Thus they should not be viewed as limiting to the scope of the present teachings.

In one embodiment, the first treatment location (202) is on the ventricular free wall near the ventricular septum, the second treatment location (242) is also on the ventricular free wall near the ventricular septum opposite from the first treatment location (202). According to another embodiment, a third location is somewhere between the first and second treatment locations (242) on the ventricular free wall. One skilled in the art should understand the specific locations disclosed here are not meant to limit the scope of the present teachings, but merely facilitate to the understanding of present disclosure. Other treatment location could also be used with devices and methods described herein.

Thus, upon reducing the distance between the treatment locations on the ventricular free wall, the right ventricle (10) is reshaped and resized. In one embodiment, the reduction in distance between the three locations on the ventricular free wall is configured so that the reduction in the right ventricle (10) sphericity index, is within 25-40%, and/or the tricuspid valve (8) tethering height is within 4-10 mm. In another embodiment, the distance between at least two locations on the ventricular wall is roughly 50% of the initial distance between the at least two treatment locations.

In yet another embodiment, the ventricular reshaping and resizing technique could also be used by tensioning a papillary muscle to the ventricular free wall, tensioning a papillary muscle to the ventricular septum, or tensioning a ventricular free wall to a ventricular septum etc. One skilled in the art should be able to incorporate the above-disclosed technique to any location inside the right ventricle (10), in order to reshape and resize the ventricle.

Now referring to FIGS. 21-26, another exemplary embodiment of securing the papillary muscle is disclosed, where instead of deploying a tissue anchor through and across the tissue of the papillary muscle, a wire loop is wrapped about the papillary muscle.

Similar to what has been described above, a guide (50) is deployed inside the right atrium, and a first wire delivery catheter (260) is extended through the lumen of the guide (50) inside the right ventricle (10). Similar to what has been described, the distal end portion (262) of the first wire delivery catheter (260) has a bend, curve, or hook shaped arc, which is configured to wrap around the papillary muscle (28). Similar to what has been described above, for example, with reference to FIG. 4, in various embodiments, the first wire delivery catheter (260) is adapted to extend distally, retract proximally, rotate axially, and pivoted radially, or other manipulated by a clinician from outside of the body.

Figure 21:
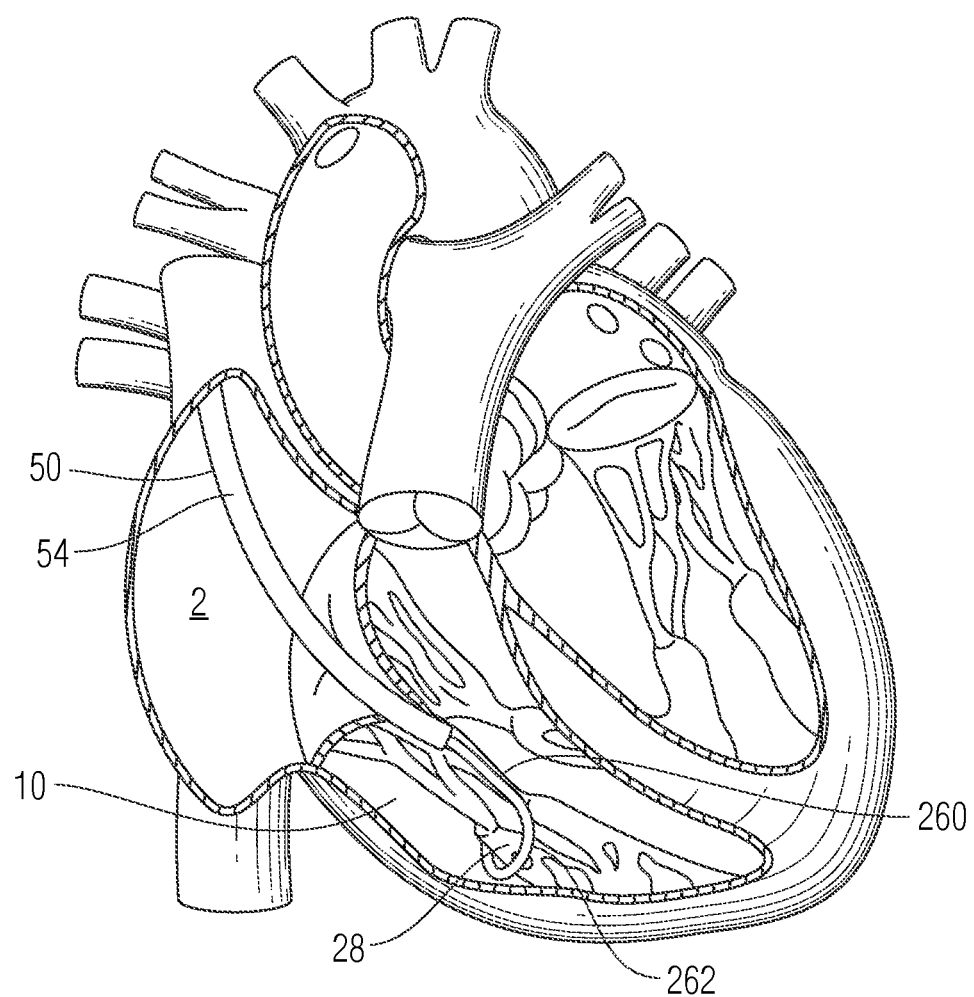
FIG. 21 is a perspective view of another exemplary wire delivery catheter directed into the right ventricle in accordance with the present teachings.

In various embodiments, the curved distal end portion (262) of the first wire delivery catheter (260) is steered to wrap about a first papillary muscle (28), as shown in FIG. 21. A clinician can confirm the positioning of the distal end portion (262) of the first wire delivery catheter (260) around the papillary muscle (28), either by visually examining the radio-opaque marker or textured surface under radiographic imaging, or by injecting a contrast media into the ventricle. Upon confirming the positioning of the distal end portion (262) of the first wire delivery catheter (260), a capture device (270) is deployed inside the right ventricle (10).

Figure 22A:
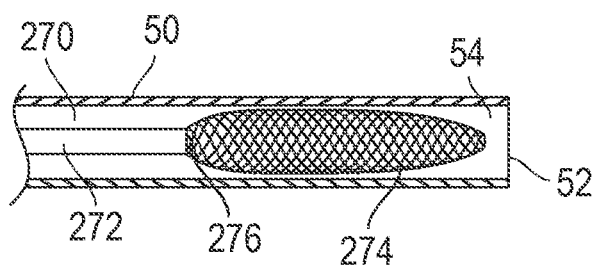
FIGS. 22a-b, 23a-b, and 24 are perspective views of an exemplary capture device in accordance with the present teachings.
Figure 22B:
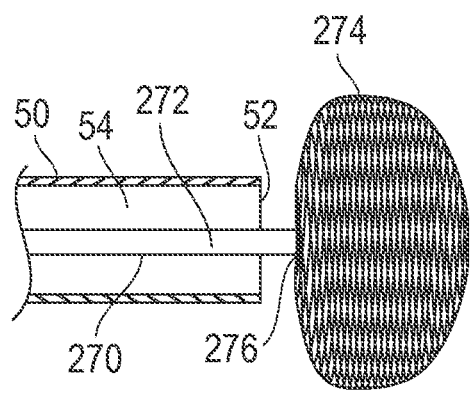

FIGS. 22a-b illustrate an embodiment with a capture device (270). According to some embodiments, a capture device (270) includes an elongated body (272) with a capture basket (274) at its distal end (276). According to some embodiments, the capture basket (274) has a radially expanded basket-like profile for capturing the wire as described below, and an elongated profile when being constrained within a sheath, such as the guide (50).

According to some embodiments, the elongated body (272) with the capture basket (274) at its distal end (276) is adapted to slide distally and proximally through the axial lumen of a sheath, such as the guide (50). As the capture basket (274) being inside the axial lumen of the sheath, the capture device (270) is in its elongated profile. FIG. 22a illustrates an embodiment of the elongated configuration of the capture basket (274) as being constrained by the guide (50). According to another embodiment, the capture basket (274) at the distal end (276) of the elongated body (272) is adapted to be pushed out of the distal end of a sheath, such as the guide (50). As the capture basket (274) extends outside of the distal end of the sheath, it resumes its expanded profile. FIG. 22b illustrates an embodiment of the expanded configuration of the capture basket (274) as the elongated body (272) of the basket (274) extends distally, and the capture basket (274) outside of the guide (50). The deployed capture basket (274) at least partially fills the volume of the right ventricle (10), as illustrated in FIG. 25. In another embodiment, the capture basket (274) at the distal end (276) of the elongated body (272) is adapted to be retracted back inside the lumen of a sheath, such as the guide (50) from its distal end. According to some embodiments, as the capture basket (274) is being retracted back into the sheath, it collapses into its elongated profile. One skilled in the art would understand that although FIGS. 22a-b illustrate that the capture device (270) used with the guide (50), a separate sheath could also be used with the capture device (270). In one embodiment, the separate sheath is slidably disposed within the guide (50). In another embodiment, the separate sheath extends along the side of the guide (50). Thus what has been described herein should not be viewed as limiting.

According to one embodiment of the present teachings, upon deployment, the radial expansion of the capture basket (274) is due to the elastic nature of the material. According to another embodiment of the present teachings, upon deployment, the radial expansion of capture basket (274) is due to its pre-set thermal shape memory of the material. According to another embodiment of the present teachings, upon deployment of the capture basket (274), it is radially expanded by the clinician, for example, with the use of a pull wire which compresses the basket longitudinally and causes the basket to expand radially.

Although the capture basket is depicted as a woven structure in FIGS. 22a-b it is understood that the capture basket could have any number of other configurations. For example, the capture basket could consist of single wire loop that forms a lasso. Alternatively, the capture basket could consist of a pair of curved wires which are crimped at the distal end to form a loop. Furthermore, the capture basket could include a series of curved wires which are each crimped together to form a basket which fills a volume. For example, the basket could include 5-7 curved wires which are spaced around the curve to form a generally spherical wire-frame.

Figure 23A:
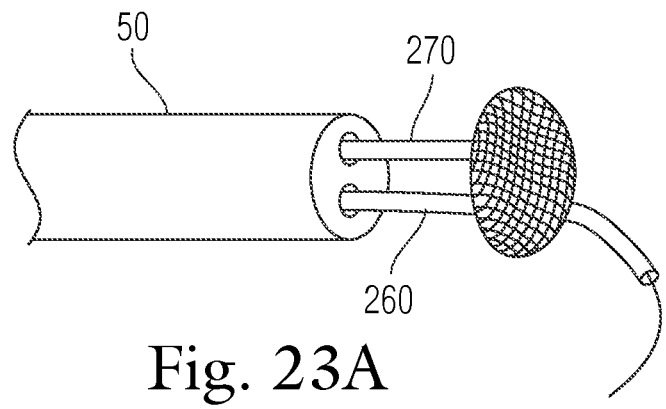
Figure 23B:
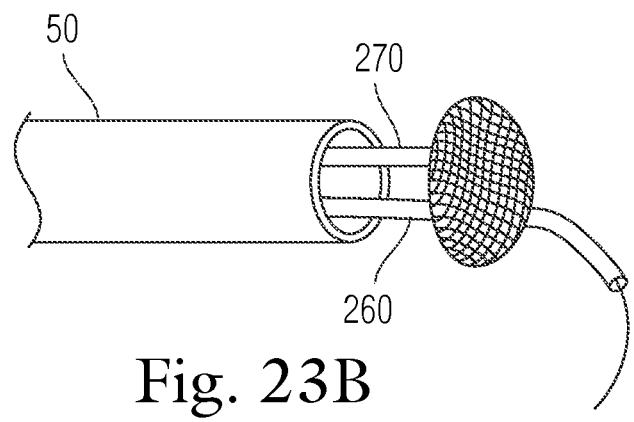
Figure 24:
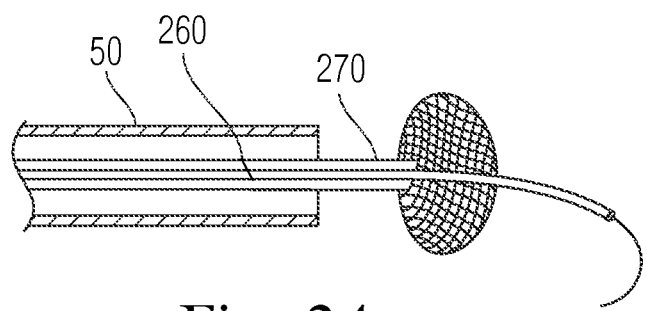

According to one embodiment, a capture device (270) having a capture basket (274) constrained to its elongated profile is directed distally through the lumen (54) of the guide (50). According to some embodiments, when a multi-lumen sheath is used as the guide (50), where the capture device (270) extends through a separate lumen from the one used by the first wire delivery catheter (260), as illustrated in FIG. 23a. According to other embodiments, when a single-lumen sheath is used as the guide (50), the capture device (270) extends side-by-side with the first wire delivery catheter (260) through the same lumen of the guide (50), as illustrated in FIG. 23b. According another embodiment, the capture device (270) includes an axial lumen extending from the proximal end of the elongated body (276) to the distal end of the capture basket (274). In one embodiment, the capture device (270) slides axially over the first wire delivery catheter (260), for example as illustrated in FIG. 24.

According to some embodiments, the movement of the capture device (270) is independent of the movement of the first wire delivery catheter (260). As the distal end portion (262) of the first wire delivery catheter (260) wraps around the papillary muscle (28), a clinician can then deploys the capture basket (274). According to other embodiments, the movement of the capture device (270) is dependent to the movement of the first wire delivery catheter (260). Thus, as the distal end portion (262) of the first wire delivery catheter (260) wraps around the papillary muscle (28), the capture basket (274) is configured to extend outside of the guide (50) and deploy inside the right ventricle (10) at the same time.

Figure 25A:
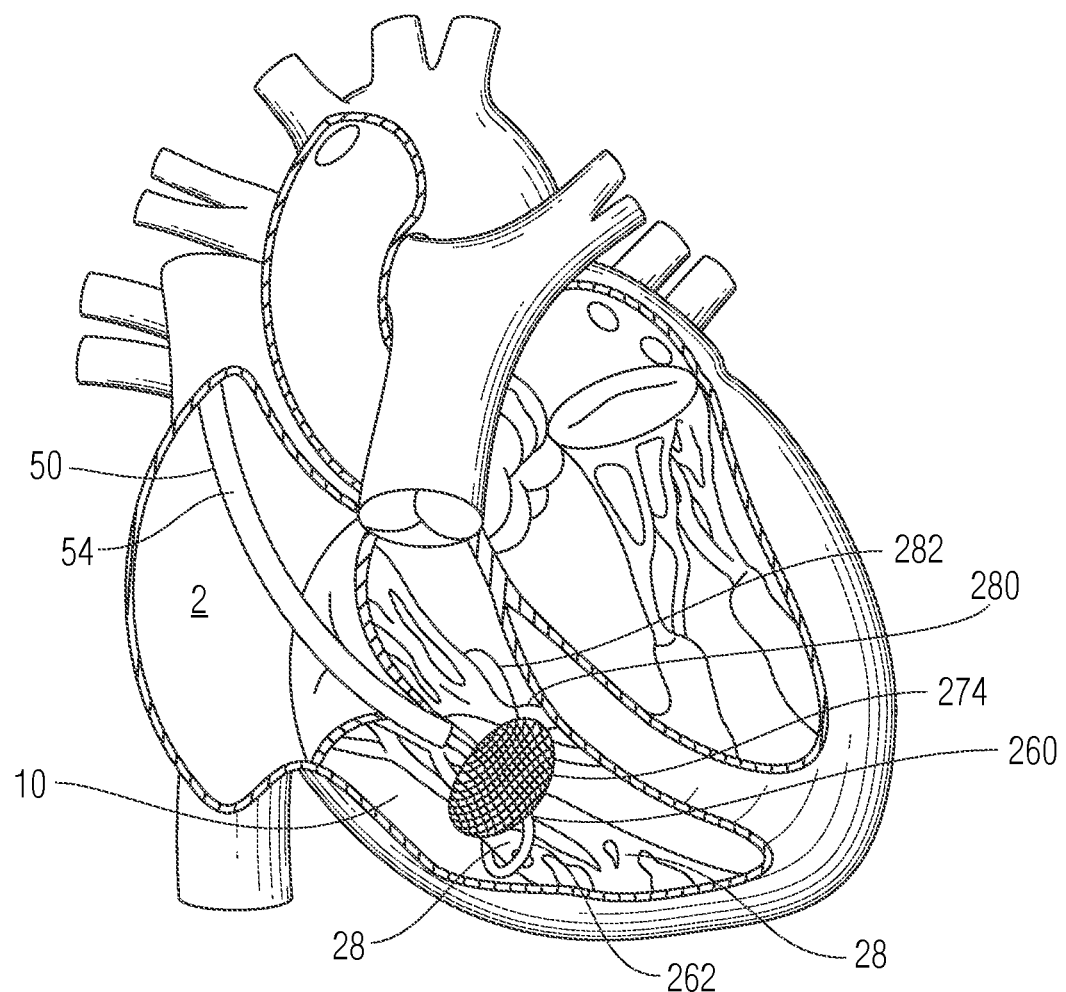
FIGS. 25a-25b are perspective views of an exemplary wire captured and pulled through the guide in accordance with the present teachings.
Figure 25B:
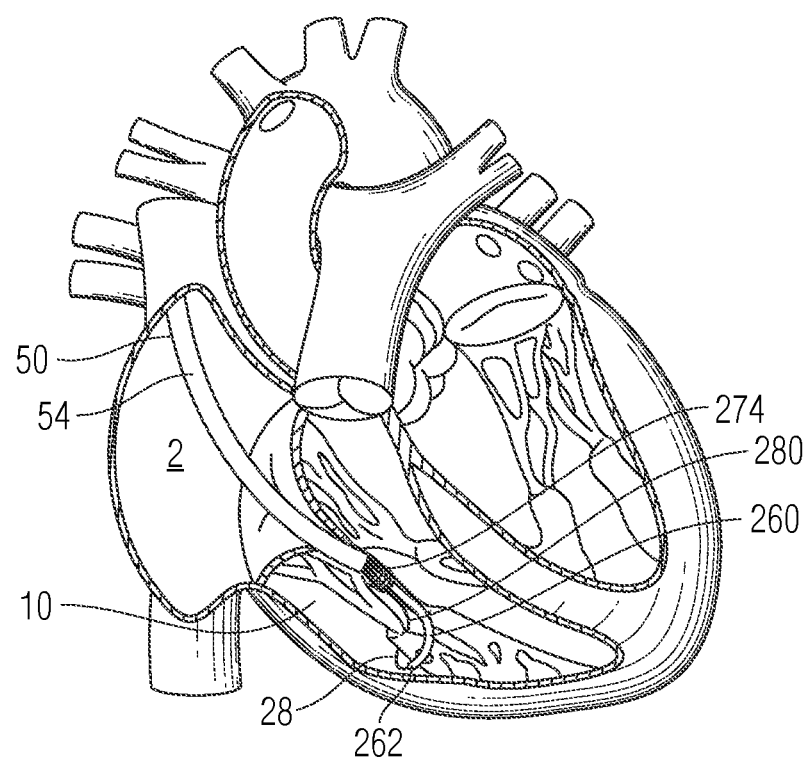
Figure 26:
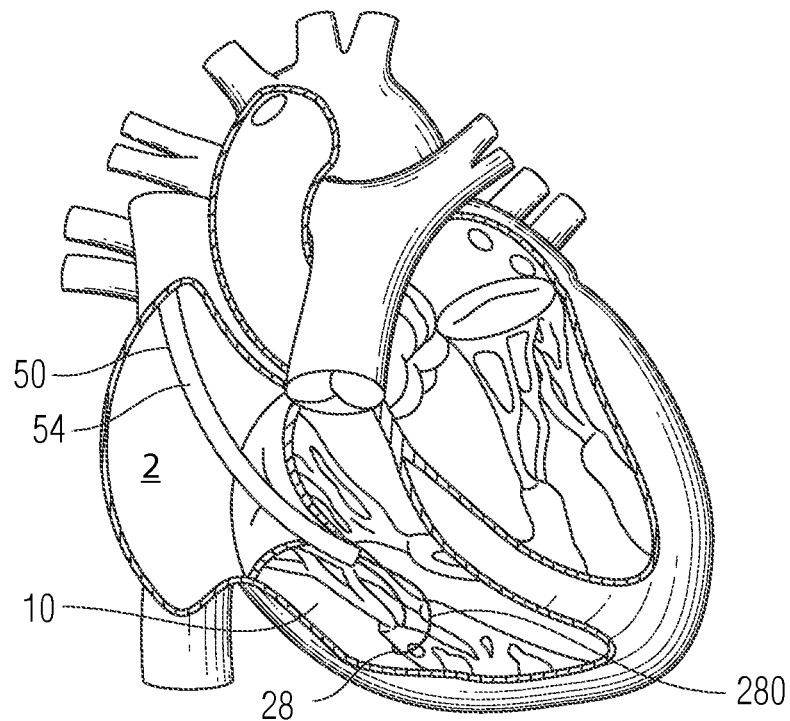
FIG. 26 is a perspective view of an exemplary wire deployed around a papillary muscle in accordance with the present teachings.

Now referring to FIGS. 25a-b, a wire loop (288) is deployed wrapping about the papillary muscle (28). As the distal end portion (262) of the first wire delivery catheter (260) is properly wrapped around the first papillary muscle (28), the capture basket (274) deploys inside the right ventricle (10) as illustrated in FIG. 25a. A first wire (280) then extends distally with its distal portion (282) exiting the distal end (264) of the first wire delivery catheter (260), and entering the right ventricle (10) and the space filled by the deployed the capture basket (274), as illustrated in FIG. 25a. The distal portion (282) of the first wire (280) is then captured by the capture basket (274). As a clinician retracts the capture basket (274) proximally back into the sheath or the guide (50), the capture basket (274) collapses onto the distal portion (282) of the first wire (280), as illustrated in FIG. 25b. As the clinician further retracts the capture device (270) proximally, the capture device (270) pulls the distal portion (282) of the first wire (280) proximally through the lumen (54) of the guide (50) and out of the body. As a result, as illustrated in FIG. 26, as one end of the wire (280) remains outside of the body, the other end of the wire extends through the guide (50), inside the right ventricle (10), wrapping around the first papillary muscle (28), then extends proximally through the guide (50), outside of the body.

Figure 27A:
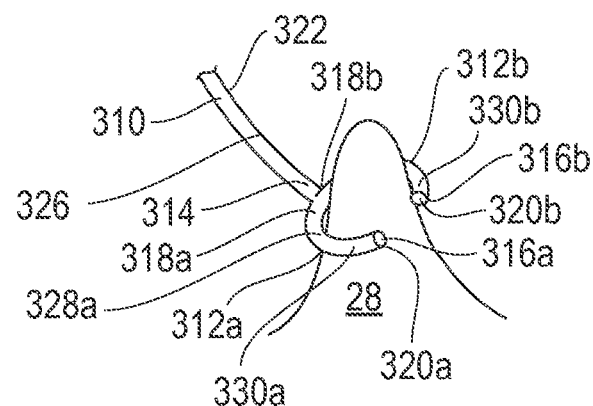
FIGS. 27a-27b are perspective views of another exemplary wire delivery catheter in accordance with the present teachings.
Figure 27B:
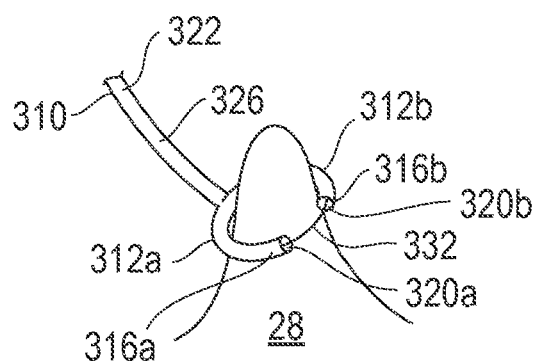

FIGS. 27a-b illustrate another example of wire capturing mechanism, where a wire delivery catheter (310) has two separating halves (312a, 312b). The wire delivery catheter (310) has an elongated body (322) with a proximal end (not shown), a distal end (314), and an axial lumen (326) extending through. Each separating halves (312a, 312b) has a free end (316a, 316b) and a fix end (318a, 318b) with a lumen (320a, 320b) extending through the free end and the fixed end. The lumens (320a, 320b) of the two separating halves (312a, 312b) connect with the axial lumen (326) of the elongated body (322). As shown in FIG. 27a, the proximal portions (328a, 328b) of the two separating halves (312a, 312b) curve distally and radially outward from the longitudinal axis of the elongated body (322), and then the distal portions (330a, 330b) of the two separating halves (312a, 312b) curve distally and radially inward from its proximal portion to its free ends (316a, 316b). Similar to what has been described above, in some embodiments, the radial curves are achieved by a pre-formed configuration. During delivery, the two separating halves (312a, 312b) are constrained by a separate catheter/sheath, such as the guide (50). Once freed from the constraint, the two separating halves (312a, 312b) resume their pre-formed radially outward configuration. In alternative embodiments, the radial pivoting of the two separating halves (312a, 312b) is achieved by an actuation mechanism controlled by a clinician from outside of the body. Similar to what has been described above, for example, with reference to FIG. 11, two separating halves (312a, 312b), adapted to be positioned against the opposite side of the papillary muscle (28).

FIG. 27a illustrates the two separating halves (312a, 312b) of the wire delivery catheter positioned around a papillary muscle (28), with each separating halves (312a, 312b) on the opposite side. A wire (332) extends from the proximal end of the lumen (326) of the wire delivery catheter (310) distally, reaching the lumen (320a) of the half (312a), further extends distally, existing the free end (316a). As the clinical continues pushing the wire (332) distally, the distal end (334) of the wire (332), loops back, enters of the free end (316b) of the other half (312b), and further extends proximally through the lumen (326) of the wire delivery catheter (310) to the outside of the body. According to some embodiments, the two separating halves (312a, 312b) and the wire (332 are configured in such way to ensure that the distal end (334) of the wire (332) enters the other distal end of the other half upon existing the distal end of one half.

According to one embodiment of the present teachings, when both end of the wire (332) are outside of the body, the wire delivery catheter (310) retracts proximally. As a result, as illustrated in FIG. 27b, similar to what has been described with reference to FIG. 26, as one end of the wire (332) remains outside of the body, the other end of the wire extends through the guide (50), inside the right ventricle (10), wrapping around the first papillary muscle (28), then extends proximally through the guide (50), outside of the body. The end result of this placement of the wire is that a wire path is formed around the papillary muscle with both ends of the wire externalized outside of the body.

Although two wire capture embodiments have been described herein, one with reference to FIGS. 22-24, and the other with reference to FIG. 27a, one skilled in the art would understand that other capture devices can also be used without departing from the spirit of the present teachings. Thus the disclosure should not be viewed as limiting.

Figure 28:
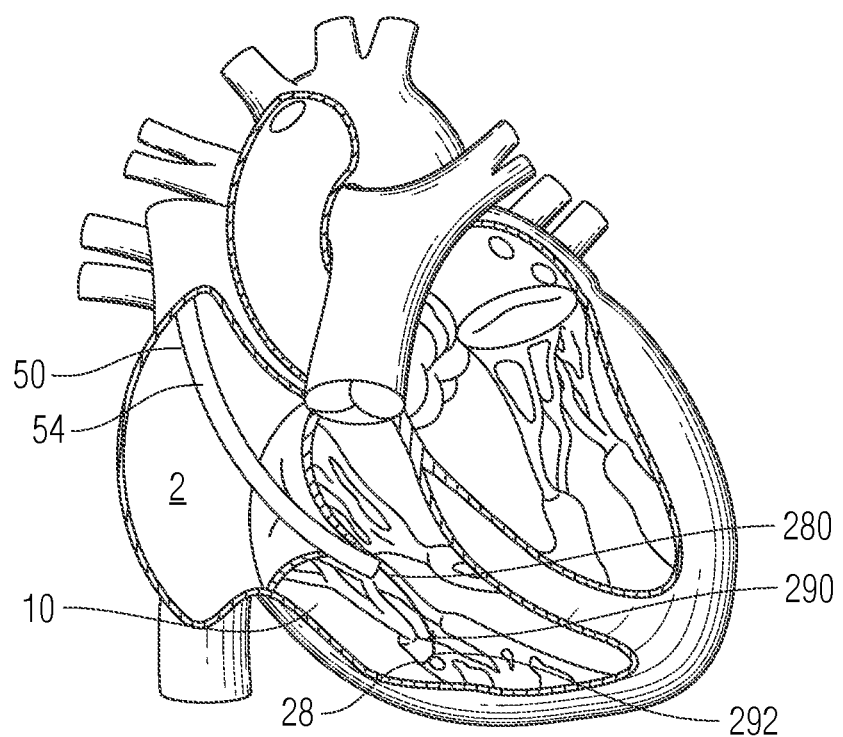
FIG. 28 is a perspective view of an exemplary loop deployed around a papillary muscle in accordance with the present teachings.

At this point, according to one embodiment of the present teachings, a clinician forms a slip knot (290) with one end, and has the other end of the wire (280) sliding through the slip knot (290). By pulling the free end of the wire (280) proximally, the slip knot (290) slides over the wire (280) distally forming a firm wire loop (292) around the first papillary muscle (28), as illustrated in FIG. 28. In one embodiment, as the wire (280) is being pulled further proximally, the wire loop (292) is tightened around the papillary muscle (28).

In some embodiments of the present teachings, the wire incorporates certain features that prevent the wire from over-compressing or dissecting the papillary muscle. For example, the slip knot has a pre-defined stopping point, such as a crimped section of the wire or a bulge on the wire, preventing the wire from dissecting or over-compressing the papillary muscle. In another example, the wire has a series of sinusoidal curves incorporated into the wire, thereby giving the wire some degree of compliance and allowing the wire to act as a spring. In still other exemplary embodiment, the wire has a helical or spiraled section which rests against the papillary muscle acting as a spring, which limits the amount of compression that can be applied to the papillary muscle.

In still another embodiment, the wire is attached to a fabric mesh, which connects the length of a suture, or to another tensioning member. This tensioning member can be secured separately by a locking implant similar to the locking implant described above. In still other embodiments the wire is a suture, fabric mesh, or polymeric tensioning member. Although in the above and continuing discussing the term wire loop is used, it is understood that one skilled in the art could substitute the wire loop for a suture loop, fabric loop, cable, spring, mesh, monofilament, elongated collagen tensioning member, elongated mammalian tissue tensioning member, or any other similar elongated tensioning member.

Figure 29:
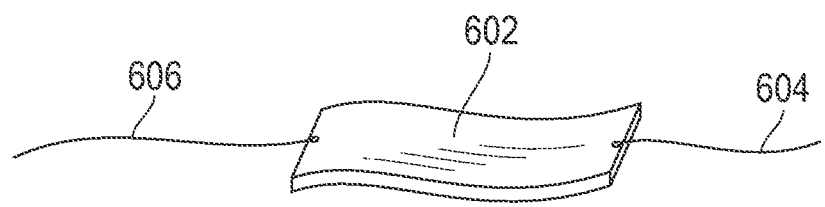
FIG. 29 is a perspective view of an exemplary fabric implant in accordance with the present teachings.
Figure 30:
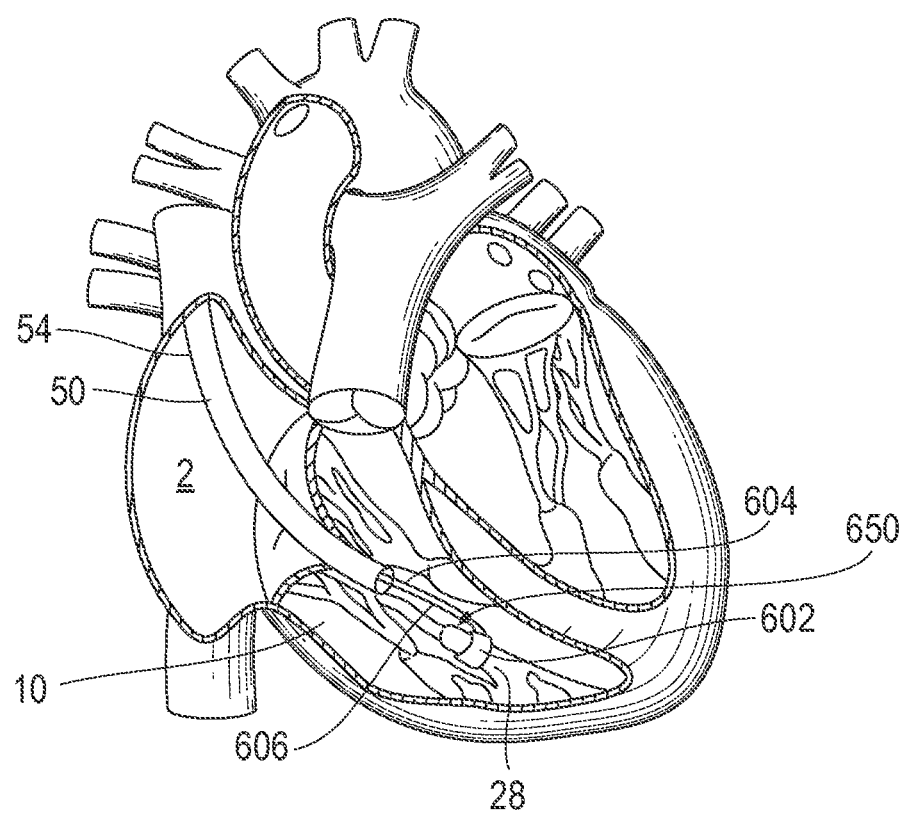
FIG. 30 is a perspective view of an exemplary fabric implant deployed around a papillary muscle in accordance with the present teachings.

One skilled in the art should understand, other mechanism could also be incorporated here to form a loop around the first papillary muscle (28), FIG. 29-30 illustrate another embodiment of the present teachings, where a fabric implant (602) is wrapped around the first papillary muscle (28). FIG. 29 illustrates an exemplary embodiment of a fabric implant (602). Such fabric implant (602) has an elongated profile, with both ends connecting to a tension member (604, 606), and one end configured to attach to an implanting wire (280) as later described. The length of the fabric implant (602) is suitable to wrap around a papillary muscle. For example, the fabric implant (602) could have a generally rectangular side-section, with a thickness of 0.25-1.0 mm, a width of 2.5-5 mm, and a length of 15-20 mm. The width of the fabric implant (602) help spread the compression force out along the tissue surface of the papillary muscle. One skilled in the art should understand that although the side profile of a fabric implant (602) shown in FIG. 29 is general rectangle, other shapes, such as oval, hour-glass, could all be used. Thus the specific exemplary embodiment disclosed here should not be viewed as limiting.

To implant such fabric implant (602) in place, an implanting wire (280) is first looped around the first papillary muscle (28) as described above, with both ends of the wire externalized, for example as illustrated in FIG. 26. At this point, a fabric implant (602) could be attached to one end of the wire (280). A clinician then pulls the other end of the wire (280) proximally so that the fabric implant (602) is positioned around the first papillary muscle (28), and the tension member extending from the fabric implant (602) with both ends of the tension member (604, 606) remaining outside of the body. Alternatively, one end of the implanting wire is attached to the free end of one of the tension members (604, 606) connecting to the fabric implant (602). The implanting wire (280) is then pulled until the fabric implant (602) resting against the tissue surface of the papillary muscle (28), with both end of the tension member (604, 606) staying outside of the body. A suture lock (650), similar to the one described above, for example with reference to FIGS. 14 and 19, is then implanted to joins both tension members (604, 606) and thereby producing a secured fabric implant (602) loop around the first papillary muscle (28), as illustrated in FIG. 30.

In some embodiments, the surface of the fabric implant (602) has a series of barbs or hooks, configured to engage the papillary muscle, and thereby preventing migration of the implant vertically along the tissue surface of the papillary muscle. The barbs or hooks may be directional, such that on half of the implant the barbs face one direction, and on the other half of the implant the barbs face the opposite direction. This could have the effect of securing/fixing the implant against the tissue surface of the papillary muscle once sufficient tension is applied to the fabric implant (602). In one embodiment, the barbs or hooks are attached to the fabric implant (602) via any suitable means, such as braided or sewn into the fabric. The barbs or hooks barbed may be manufactured via many means known to those skilled in the art, for example, from a 0.3 mm monofilament with barbs cut directly into the filament, from a series of 0.25 mm steel hooks, or by micro-injection molding an elongate barbed tube. In another embodiment, the fabric implant (602) may incorporate one or more radio-opaque marker bands for visualization.

In one embodiment of the present teachings, the use of the fabric implant (602) looping around the papillary muscle allows a clinician to control the amount of tension on the papillary muscle. In one embodiment of the present teachings, the force imposed to the papillary muscle by the fabric implant (602) described above could be configured to extend the tissue surface of the papillary muscle. For example, the fabric implant (602) is configured to "squeeze" the papillary muscle along its contact surface with the papillary muscle, and which could lead to an increase in the length/height of the papillary muscle by 2-4 mm. Such increase in the length/height of the papillary muscle could also lead to a reduction in tricuspid valve tethering height by a similar amount.

Figure 31:
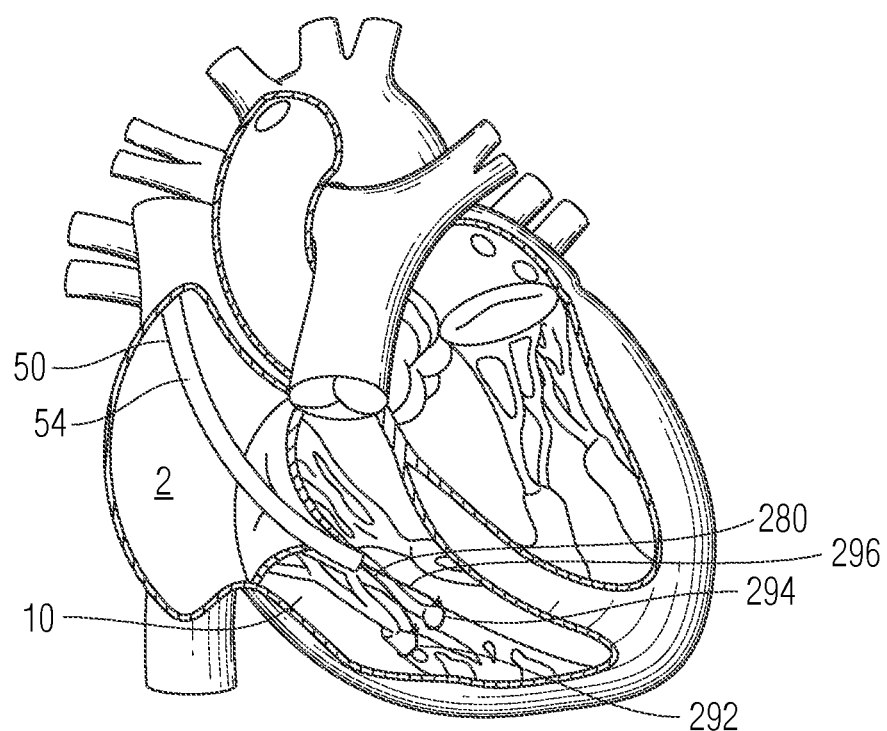
FIG. 31 is a perspective view of two exemplary loops deployed around two papillary muscle in accordance with the present teachings.

Upon securing the first papillary muscle (28) with a firm wire/fabric loop, a clinician can then deploy a second wire/fabric loop around the second papillary muscle (28) in a manner similar to what has been described above with reference to FIGS. 21-30. FIG. 31 illustrates two papillary muscles being secured to two loops (292, 294), respectively. The free ends (not shown) of the two wire/tension member (280, 296) extends proximally through the guide (50) to the outside of the body. The two free ends of the two wire/tension member (280, 296) are controlled by the clinician.

Similar to what has been described above, according to one embodiment, the first and second wire/fabric loops are at or near the base of the first and second papillary muscles. Alternatively, the first and second wire/fabric loops are at or near the middle portion of the first and second papillary muscle. In some embodiments, the first and second wire/tension member (280, 296) extend under the bridge formed by the trabeculae carneae (32), and the first and second w wire/fabric loops are formed around the trabeculae carneae (32). One skilled in the art would understand that any two of the three papillary muscles, the posterior, the anterior, and the septal papillary muscles, could be secured by the first and second wire/fabric loops. In addition, all three papillary muscles can be secured to three wire/fabric loops respectively and individually according to the manner described above, such as with reference to FIGS. 21-32.

Figure 32:
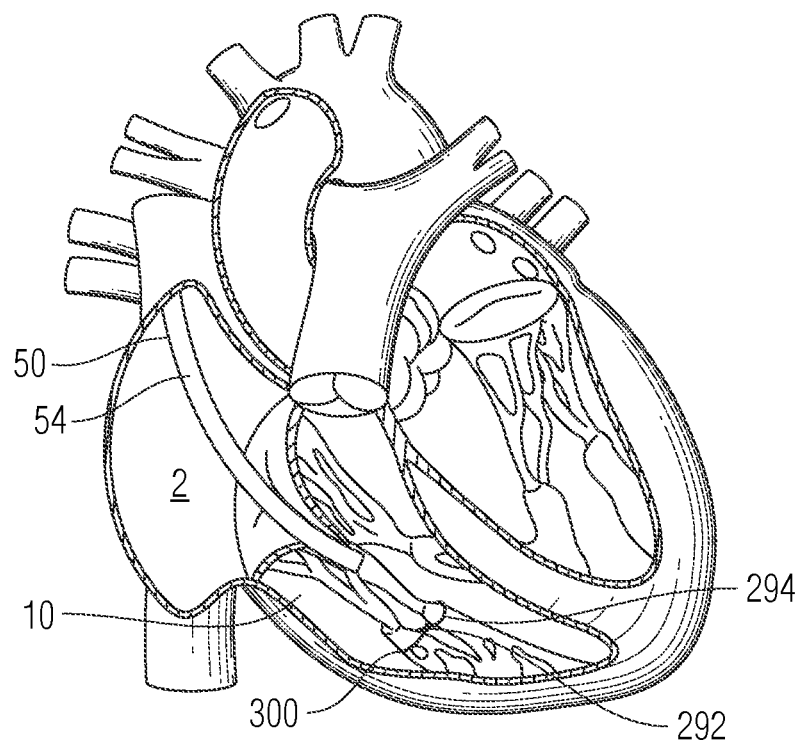
FIG. 32 is a perspective view of an exemplary loop-lock system deployed inside the right ventricle in accordance with the present teachings.

To reshape and resize the right ventricle (10), similar to what has been described above according to FIG. 12, a clinician applies tension to one or both of the wire/tension member (280, 296). This tension pulls two wire/fabric loops closer to each other, thereby reducing the distance between the two papillary muscles. This tension, and the reduced distance between the two papillary muscles, are maintained by directing a suture lock (300) along the wire/tension member (280, 296) towards the papillary muscles, as illustrated in FIG. 32. Upon reducing the distance between the two papillary muscles, the right ventricle (10) is reshaped and resized. Similar to what has been described above, in one embodiment, the reduction in distance between the two papillary muscles is configured so that the reduction in right ventricle sphericity index is within 25-40%. In another embodiment, the reduction in distance between the two papillary muscles is configured so that the reduction in the tricuspid valve tethering height is within by 4-10 mm. In another embodiment, the distance between the two papillary muscles is reduced from the initial separation of the papillary muscles by roughly 30-50% of the distance.

According to one embodiment, the suture lock (300) is positioned close to the first papillary muscle. In another embodiment, the suture lock (300) is positioned close to the second papillary muscle. In an alternative embodiment, the suture lock (300) is positioned somewhere between the first and second papillary muscle.

In one embodiment, the first and second papillary muscles are anterior and posterior papillary muscle. In another embodiment, the first and second papillary muscles are anterior and septal papillary muscle. In yet another embodiment, the first and second papillary muscles are posterior and septal papillary muscles.

Although FIG. 32 illustrates that two papillary muscles are secured and tensioned together by the above described wire/fabric loop-suture lock system, one skilled in the art should understand that three papillary muscles can also be secured and tensioned together by the above described wire/fabric loop-suture lock system. In yet another embodiment, the first papillary muscle is secured and tensioned to second papillary muscle by the above described the wire/fabric loop-suture lock system, and the second papillary muscle is secured and tensioned to the third papillary muscle by the above described wire/fabric loop-suture lock system, similar to illustration in FIGS. 14a-c.

Figure 35A:
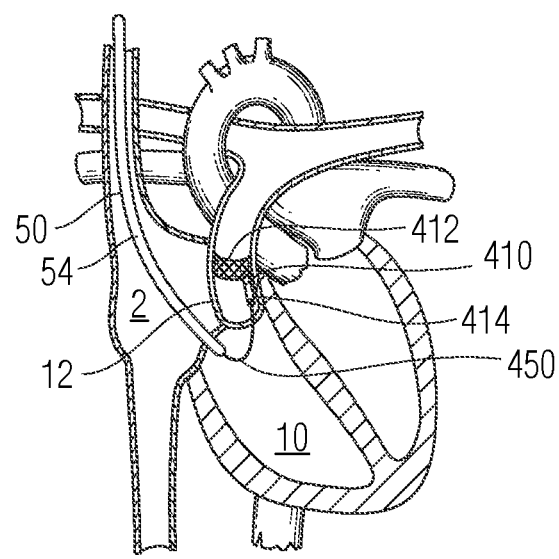
FIGS. 35a-35b are perspective views of an exemplary stent tissue anchor deployed near the pulmonary valve in accordance with the present teachings.
Figure 35B:
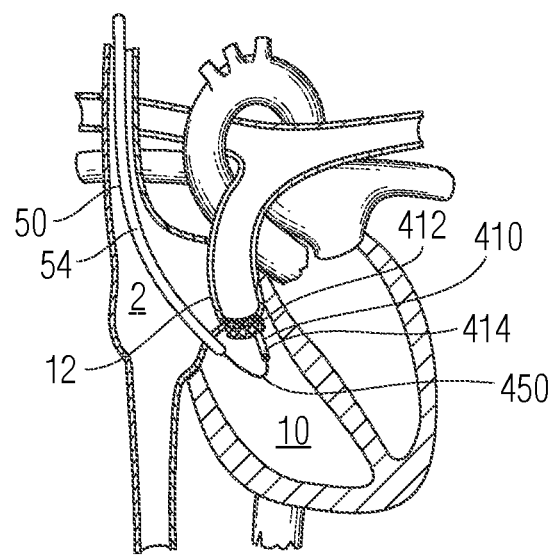
Figure 36:
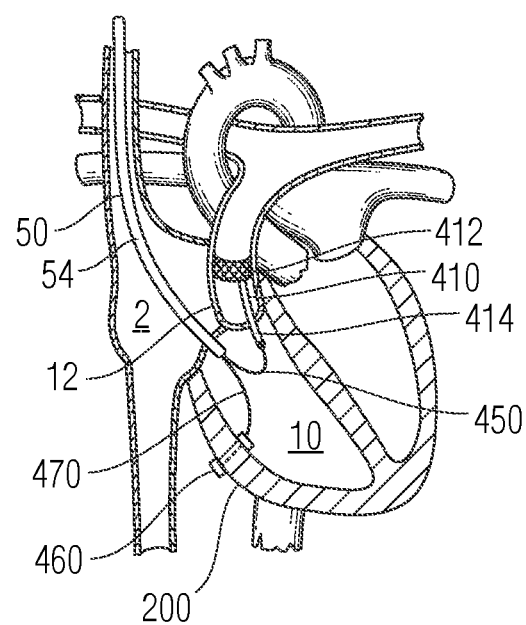
FIG. 36 is a perspective view of another exemplary tissue anchor deployed at a treatment location inside the right ventricle in accordance with the present teachings.
Figure 37:
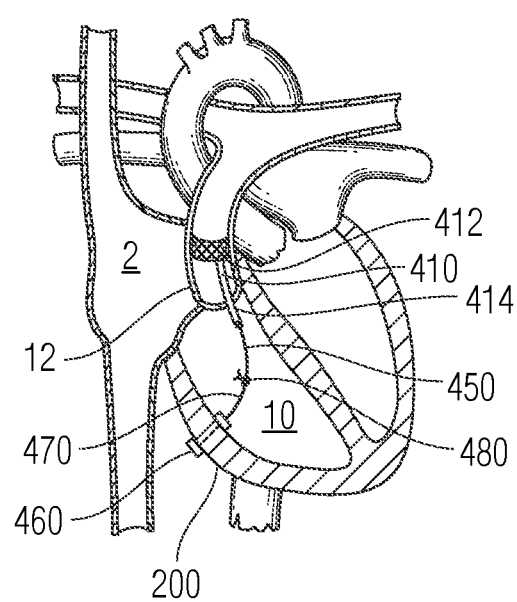
FIG. 37 is a perspective view of an exemplary stent tissue anchor-tissue anchor-lock system deployed inside the right ventricle in accordance with the present teachings.

Now referring to FIG. 33-37, right ventricular resizing and reshaping is achieved by another anchor-lock (400) system, according to various embodiments of the present teachings. FIG. 36 illustrates a stent tissue anchor (410) deployed at or near the pulmonary valve (12) with a suture connecting to the proximal end of the stent tissue anchor (410), a tissue anchor deployed on the ventricular free wall opposite to the pulmonary artery also with a suture connecting to the proximal end of the tissue anchor, and suture lock (150) secures the two anchors while maintaining the tension between the anchors.

Figure 33A:
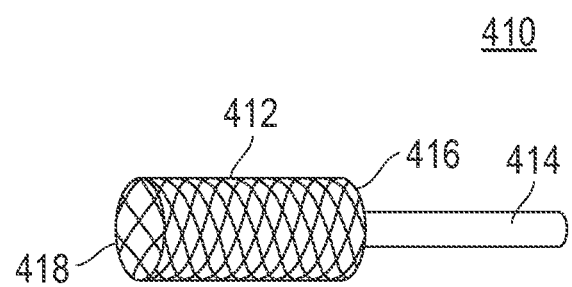
FIGS. 33a-33b are perspective views of an exemplary stent tissue anchor in accordance with the present teachings.

According to one embodiment of the present teachings, as illustrated in FIG. 33a, the stent tissue anchor (410) has a radially expanded deployed configuration, where, the stent tissue anchor (410) has an elongated tubular body (412) and a proximal tab (414) at the proximal end (416) of the elongated tubular body (412). In this embodiment, the elongated tubular body (412) has a general tubular profile, with an axial lumen (418) and an open-mesh like surface areas which allow the stent tissue anchor (410) to collapse in or a smaller radial profile during a percutaneous delivery. The surface of the elongated tubular body (412) has a pre-cut or pre-formed pattern which is configured to allow radially expansion or contraction of the stent tissue anchor (410) for percutaneous delivery and deployment. Specifically, upon deployed at a treatment site, the elongated tubular body (412) expands radially, and the pre-cut or pre-formed pattern on the tubular surface of the stent tissue anchor (410) creates an open-mesh structure with hollowed area. According to one embodiment of the present teachings, the size of each opening on the tubular surface ranges from 1 mm$^2$ to 5 mm$^2$.

According to another embodiment of the present teachings, the opening area consists of 50-95% of entire tubular surface.

In one embodiment of the present teachings, upon deployment, the stent tissue anchor (410) expands radially due to the elastic nature of the material. In another embodiment, such radial expansion is achieved by the pre-set thermal shape memory of the material. In yet another embodiment, such radial expansion is achieved manually via an inflating balloon.

In the embodiment of the presenting teachings where the stent tissue anchor (410) is expanded in vivo via a balloon, the stent tissue anchor (410) can be mounted over a balloon catheter, where the inflatable balloon is positioned inside the elongated tubular body (412) of the stent tissue anchor (410). Upon positioning the stent tissue anchor (410) at the treatment site, the balloon is then inflated, and the inflated balloon expands the elongated tubular body (412) of the stent tissue anchor (410) to a desired size. Then, the balloon is deflated and retracted out of the body.

According to one embodiment of the present teachings, a deployed stent tissue anchor (410) is configured to secure itself against the surrounding tissue. In one embodiment, the stent tissue anchor (410) is secured at the treatment site by a radial interference force. In this embodiment, the pre-fabricate configuration of at least a portion of the deployed stent tissue anchor (410) has a greater radial dimension than the interior of the treatment location which produces an interference fit between the stent tissue anchor (410) and the surrounding tissue. According to another embodiment of the present teachings, the stent tissue anchor (410) has at least one barb like feature for securing the stent tissue anchor (410) against surrounding tissues. Such barb like feature can reduce relative movement of stent tissue anchor (410) against the surrounding tissue, reduce the chance of stent tissue anchor (410) embolization, and/or reduce tissue abrasion. In one embodiment, the stent tissue anchor (410) has at least one barb like feature at or near its distal or proximal end. In other embodiment, the stent tissue anchor (410) has multiple tissue anchors along its tubular surface configured to secure the stent tissue anchor (410) to the treatment location, for example, inside the right ventricle outflow track, or inside the pulmonary artery, etc. It should be understood by those with ordinary skill in the art that location of the barb like feature on the stent tissue anchor (410), and securement location depending on the treatment site, size of the stent tissue anchor (410), and needs for securement. In one exemplary embodiment of the present teachings, the barb like feature could be hook, grasper, loops, ring, spine, tine, helix, barb, clip, or one or more other features known to those skilled in the art to penetrate into tissue around the exterior of the tubular surface.

Figure 33B:
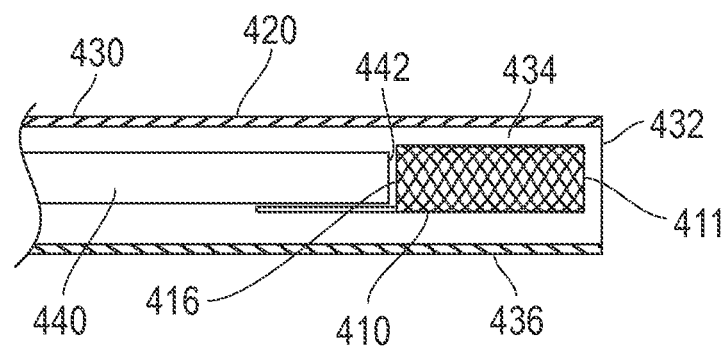

According to another embodiment of the present teachings, as illustrated in FIG. 33b, the stent tissue anchor (410) has a collapsed elongated delivery configuration with a delivery system (420). In one embodiment, the stent tissue anchor (410) delivery system (420) includes a delivery sheath (430) having a distal end (432), a proximal end (not shown), and an axial lumen (434), and a delivery catheter (440) slidably disposed within the lumen (434) of the delivery sheath (430). Both the delivery sheath (430) and the delivery catheter (440) can be manipulated by a clinician from outside of the body. In this particular embodiment, a stent tissue anchor (410), extended into its elongated delivery profile, is slidably disposed within a distal portion (436) of the delivery sheath (430). In one embodiment, the distal end (411) of the stent tissue anchor (410) is within the distal end (432) of the delivery sheath (430), the proximal end (416) of the stent tissue anchor (410) is in contact with the distal end (442) of the delivery catheter (440), and the distal end (442) of the delivery catheter (440) is designed so as to contact the proximal end (416) of the stent tissue anchor (410), preventing it from moving proximally, or pushing the stent tissue anchor (410) distally during deployment.

In one embodiment of the present teachings, the distal end (442) of the delivery catheter (440) contacts but does not engage the proximal end (416) of the stent tissue anchor (410) in such a way that allows the delivery catheter (440) to push the stent tissue anchor (410) distally, and prevent stent tissue anchor (410) from sliding proximally during deployment. After the stent tissue anchor (410) fully exits the delivery sheath (430), the delivery catheter (440) no longer manipulates the stent tissue anchor (410). In this embodiment, once the stent tissue anchor (410) outside the delivery system (420), it is no longer controlled by the clinician.

In another embodiment of the present teachings, the delivery catheter (440) actively attaches the stent tissue anchor (410) during delivery and implantation. Such attachment can be achieved by mechanical means, magnetic means, or other methods known to those skilled in the art. For example, the attachment between the delivery catheter (440) and stent tissue anchor (410) can be in the form of any operator controlled mechanism, such as a threaded attachment, a ball and socket attachment, a ball and loop attachment, a ball-to-ball attachment, a pin-to-pin attachment, a tensioned clamp and ball attachment, a collet and ball attachment, a magnetic attachment member, or a releasable suture. Such attachment requires releasing the stent tissue anchor (410) by a clinician in order to free the stent tissue anchor (410) from the delivery system (420). In this embodiment, after the stent tissue anchor (410) fully exits the delivery sheath (430), the proximal end (416) of the stent tissue anchor (410) is still been held by the delivery catheter (440) which allows a clinician to assess the deployment, the performance, and the securement of the stent tissue anchor (410) to the surrounding tissue. When the deployment is deemed satisfactory, the clinician can then release the stent tissue anchor (410) and remove the delivery system (420) including delivery sheath (430) and delivery catheter (440) from the body. If the deployment is not satisfactory, the clinician can remove the stent tissue anchor (410) by pulling the stent tissue anchor (410) proximally back into the delivery sheath (430), and then remove the delivery system (420) including delivery sheath (430) and delivery catheter (440) along with the stent tissue anchor (410) from the body.

In one embodiment, the attachment between the delivery catheter (440) and stent tissue anchor (410) is reversible. That is, the delivery catheter (440) and the stent tissue anchor (410) can re-attached after the stent tissue anchor (410) was partially or completely released from such attachment. One skilled in the art should understand that the connection/attachment between the delivery catheter (440) and the stent tissue anchor (410) could be any mechanism known in the field. Thus, what has been described herein should not limit the scope of the present teachings.

According to one embodiment of the present teachings, the stent tissue anchor (410) device in whole or portion(s) may be made of a biocompatible metal or polymer. In some embodiments, the device in whole or portion(s) is made of an elastic material, super-elastic material, or shape-memory alloy which allows said portions to distort into a generally straightened profile during the delivery process and resume and maintain its intended profile in vivo once it is deployed from the delivery catheter. In some embodiments, the device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys or other metallic alloys. Alternatively, in such embodiments, part or all of the device is made of a polymer such as PTFE, UHMPE, HDPE, polypropylene, polysulfone, or other biocompatible plastic. The surface finish of the device is textured to induce tissue response and tissue in-growth for improved stabilization. Alternatively, part or all of the device can be fabricated from a resorbable polymer such as polyactic acid, polyglycolic acid, polycaprolactone, a combination of two or more of these or a variety of other resorbable polymers that are well known to those skilled in the art.

According to one embodiment of the present teachings, radio-opaque marker is used to make the device visible using radiographic imaging equipment such as X-ray, magnetic resonance, ultrasound or other imaging techniques. Marker as disclosed herein may be applied to the ends of any part of the devices, or even on the delivery system of the device. A radio-opaque marker can be sewed, adhered, swaged riveted, otherwise placed and secured on the device. The radio-opaque marker may be formed of tantalum, tungsten, platinum, iridium, gold, alloys of these materials or other materials that are known to those skilled in the art. The radio-opaque marker can also be cobalt, fluorine or numerous other paramagnetic materials or other MR visible materials that are known to those skilled in the arts.

In some embodiments of the present teachings, the pre-cut or pre-formed pattern on the tubular surface of the stent tissue anchor (410) device is fabricated by laser-cutting or acid-etching a pattern onto a preformed tube. In other embodiments, the pre-cut or pre-formed pattern on the tubular surface of the device is fabricated by slotted using, for example, a machining laser or water drill or other method and then expanded to form the open structure. Such preformed tube is then shape-set to the intended deployed configuration. Alternatively the pre-cut or pre-formed pattern on the tubular surface of the device is fabricated by cutting a pattern from sheet. Such preformed sheet is then rolled up and welded or crimped at specific strut locations.

In another embodiment, the stent tissue anchor (410) device can be formed from wire that is pre-bent into the desired shape and then bonded together to connect elements either by cross-hatching, braiding, welding, or other methods of interconnecting rows of metal that are assembled into a tube-like structure. In one embodiment, the wires could be welded using a resistance welding technique or an arc welding technique, preferably while in an inert gas environment and with cooling control to control the grain structure in and around the weld site. These joints can be conditioned after the welding procedure to reduce grain size using coining or upset forging to optimize fatigue performance.

In one embodiment of the present teachings, where the stent tissue anchor (410) device is made of elastic and resilient material such as stainless steel, or nitinol, the structure of the device can be preformed into its deployed shape, and then elastically deformed and stowed during delivery so that the shape of the device would be elastically recovered after deployment. In another embodiment of the present teachings, where the device is made of pseudoelastic shape-memory material such as nitinol, the device is manually expanded to the desired deployed size, heat set in an oven while constrained to the desired shape to memorize the desired device shape.

Figure 34:
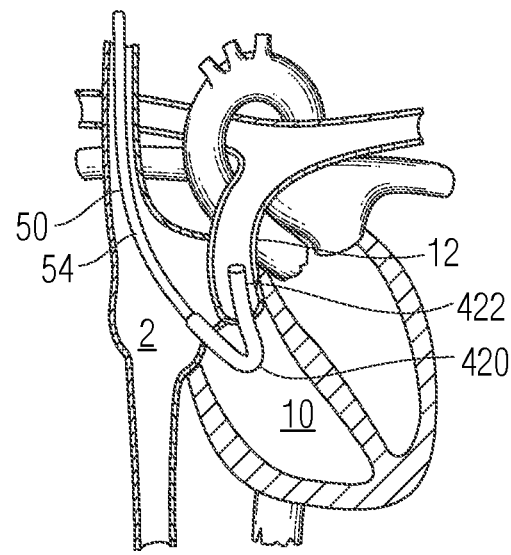
FIG. 34 is a perspective view of an exemplary stent tissue anchor delivery system directed inside the pulmonary artery in accordance with the present teachings.

FIGS. 34-35 illustrate the delivery and deployment of a stent tissue anchor (410). As illustrated in FIG. 34, in one embodiment of the present teachings, the clinician inserts a delivery system (420) holding the stent tissue anchor (410) in its delivery profile percutaneously through the guide (50) into the right ventricle (10). FIG. 34 illustrates the distal end (422) of the delivery system (420) extends distally from the right ventricle (10) through pulmonary artery, passing through pulmonary valve (12), with the distal end (422) of the delivery system (420) stopping distal to the pulmonary valve (12). In some embodiments, a radio-opaque marker(s) is used on the delivery sheath (430), the delivery catheter (440), or the stent tissue anchor (410) to aid a clinician during positioning of the delivery system (420) and the stent tissue anchor (410).

Upon satisfied with the treatment location, the stent tissue anchor (410) is then deployed. According to one embodiment of the present teachings, the delivery sheath (430) is then retracted proximally while holding the delivery catheter (440) steady to expose the stent tissue anchor (410). According to an alternative embodiment, the deployment of the stent tissue anchor (410) can be accomplished by advancing the delivery catheter (440) distally with respect to the delivery sheath (430). As the delivery catheter (440) extends distally with respect to the delivery sheath (430), the stent tissue anchor (410) is pushed outside of the distal end (432) of the delivery sheath (430). As the stent tissue anchor (410) exits the distal end (432) of the delivery sheath (430), the stent tissue anchor (410) resumes its pre-set deployed configuration.

According to one embodiment of the present teachings, once the stent tissue anchor (410) is outside of the delivery system (420), the delivery system (420) can no longer control the stent tissue anchor (410), and is then removed from the body. According to another embodiment of the present teachings, as the stent tissue anchor (410) deploys at the treatment location, the delivery catheter (440) maintains its attachment of the stent tissue anchor (410). When the deployment is deemed satisfactory, the clinician can then release the attachment between the delivery catheter (440) and the stent tissue anchor (410), and the delivery system (420) and the delivery sheath (430) and delivery catheter (440) can be removed from the body. If deployment is not satisfactory, the stent tissue anchor (410) can be retrieved via other techniques. It should be understood that the techniques disclosed for deploying the embodiments described herein are only examples. Other techniques can be used instead of, or in combination with, these disclosures. For example, the techniques used to deploy an embodiment of the devices described herein depend on the particular features of the stent tissue anchor (410), the delivery system, and the anatomy in which the stent tissue anchor (410) is being deployed.

In one embodiment, as seen in FIG. 35a, the elongated tubular body (412) of the stent tissue anchor (410) is deployed inside the pulmonary artery, distal to the pulmonary valve (12), with the proximal tab (414) of the stent tissue anchor (410) extending through the pulmonary valve (12), ending inside the right ventricle outflow track, and a suture (450) attaching to the proximal tab (414) extending proximally through the guide (50) to the outside of the body. In another embodiment, as seen in FIG. 35b, the elongated tubular body (412) of the stent tissue anchor (410) is deployed inside the right ventricle outflow track, proximal to the pulmonary valve (12), with the proximal tab (414) of the stent tissue anchor (410) extending further proximally inside the right ventricle (10), and a first suture (450) attaching to the proximal tab (414) extending proximally through the guide (50) to the outside of the body.

While maintaining the tension on the first suture (450), a clinician can then deploy a second tissue anchor (460). In one embodiment, the second tissue anchor (460) is deployed on the right ventricle wall (200) across from the right ventricle outflow track in a manner similar to what has been described above, for example such illustrated in FIGS. 15-20, or across the papillary muscle in a manner described above with reference to FIGS. 2-14, or around the papillary muscle in a manner described above with reference to FIGS. 21-32. FIG. 36 illustrates the stent tissue anchor (410) being deployed inside the pulmonary artery with its proximal tab (414) extending proximally from the elongated tubular body (412) of the stent tissue anchor (410), through the pulmonary valve (12), and being positioned inside the right ventricle outflow track, and a first suture (450) attaching to the proximal tab (414) and extending proximally through the guide (50) outside of the body. FIG. 36 also illustrates a second tissue anchor (460) deployed on the right ventricle wall (200) with a second suture (470) connecting to the second tissue anchor (460), and also extending proximally through the guide (50) outside of the body.

Similar to what has been described above, a clinician applies tension to one or both of the sutures (450, 470) of the stent tissue anchor (410) and the second tissue anchor (460). This tension pulls two anchors (410, 460) closer to each other, thereby reducing the distance between the right ventricle wall (200) and the right ventricle outflow track. This tension, and the reduced distance between the two tissue anchors (410, 460), are maintained by directing a suture lock (480) along the sutures (450, 470) towards the tissue anchors (410, 460), as illustrated in FIG. 36. Similarly, upon reducing the distance between the right ventricle wall (200) and the right ventricle outflow track, the right ventricle (10) is reshaped and resized. In addition, similar to what has been described above, the suture lock (480) could be positioned close to the proximal tab (414) of the stent tissue anchor (410). In another embodiment, the suture lock (480) could be positioned close to the second tissue anchor (460). In an alternative embodiment, the suture lock (480) is positioned somewhere between the two anchors (410, 460).

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the specification, including definitions, controls. In addition, the materials, methods, and examples are illustrative only and not intended to be limiting.

We claim:

1. A method for reshaping and resizing the right ventricle of a heart of a patient, the method comprising:
    delivering a first tissue anchor to a first papillary muscle using an implanting wire, wherein the first tissue anchor is directly attached to a first tension member and to a second tension member, wherein the first and the second tension members define a first pair of tension members, the first tissue anchor being a continuous single structure with the first and the second tension members extending laterally outward from opposing ends thereof, wherein one of: (a) the first tissue anchor and (b) one of the first and the second tension members is attached to the implanting wire;
    securing the first tissue anchor to the first papillary muscle by positioning the first tissue anchor about the first papillary muscle with free ends of the first and the second tension members being disposed external to the patient, the first tissue anchor being positioned about the first papillary muscle by movement of the implanting wire;
    securing a second tissue anchor to a second papillary muscle, wherein the first papillary muscle is located a first distance from the second papillary muscle; and
    tensioning at least one of the first and the second tissue anchors to cause the first papillary muscle to be spaced a second distance from the second papillary muscle, wherein the second distance is less than the first distance.

2. The method of claim 1, wherein each of the first and the second tissue anchors is delivered with a tissue anchor delivery catheter.

3. The method of claim 1, wherein the second tissue anchor is attached to a third tension member and to a fourth tension member, wherein the third and the fourth tension members define a second pair of tension members and the step of tensioning the at least one of the first and the second tissue anchors comprises tensioning at least one of the first and the second pairs of tension members.

4. The method of claim 3, wherein the first tissue anchor comprises a first fabric implant and the second tissue anchor comprises a second fabric implant and the first tension member and the second tension member extend outwardly from opposing ends of the first fabric implant, the third tension member and the fourth tension member extending outwardly from opposing ends of the second fabric implant for placement about the respective first and second papillary muscles.

5. The method of claim 3, further comprising a step of applying a lock member to each of the first and the second pairs of tension members to maintain the tension applied to the at least one of the first and the second pairs of tension members and to maintain the second distance between the first and the second papillary muscles.

6. The method of claim 3, wherein the third tension member and the fourth tension members are attached to opposite ends of the second tissue anchor and the step of securing the second tissue anchor to the second papillary muscle comprises the steps of: introducing a guide into a right atrium and then directing the guide through the tricuspid valve into the right ventricle; introducing the implantation wire through the guide; looping the implantation wire around the second papillary muscle with first and second ends of the implantation wire being located external to the patient; attaching the third tension member to the first end of the implantation wire; pulling the second end of the implantation wire until the second tissue anchor is positioned around the second papillary muscle and of the third and fourth tension members have lengths such that free ends of the third and fourth tension members are located external to the patient.

7. The method of claim 6, further including a step of: applying a lock member to the third and the fourth tension members, thereby securely positioning the second tissue anchor around the second papillary muscle.

8. The method of claim 3, further comprising a step of: applying a lock member to the first and the second pairs of tension members after the step of tensioning the at least one of the first and the second pairs of tension members and the distance between the first and the second papillary muscles is reduced.

9. The method of claim 1, wherein the step of securing the first tissue anchor to the first papillary muscle comprises the steps of: introducing a guide into a right atrium and then directing the guide through the tricuspid valve into the right ventricle; introducing the implantation wire through the guide; looping the implantation wire around the first papillary muscle with first and second ends of the implantation wire being located external to the patient; attaching the first tension member to the first end of the implantation wire; pulling the second end of the implantation wire until the first tissue anchor is positioned around the first papillary muscle and the first and the second tension members have lengths such that the free ends of the first and the second tension members are located external to the patient.

10. The method of claim 9, further including a step of: applying a lock member to the first and the second tension members, thereby securely positioning the first tissue anchor around the first papillary muscle.

11. The method of claim 1, wherein each of the first tissue anchor and the second tissue anchor comprises a fabric implant that has a series of barbs formed along one surface thereof.

12. The method of claim 11, wherein the series of barbs comprise a first set facing in a first direction and a second set facing in a second direction.

13. The method of claim 1, wherein each of the first tissue anchor and the second tissue anchor comprises a fabric implant that incorporates at least one radio-opaque marker band for visualization.

14. A method for reshaping and resizing the right ventricle of a heart, the method comprising:

attaching a first tissue anchor to an implant wire, wherein one end of the first tissue anchor is configured to attach to the implant wire;

delivering the first tissue anchor to a first papillary muscle by passing the first tissue anchor through a lumen formed in a tissue anchor delivery catheter;

securing the first tissue anchor to the first papillary muscle, wherein the first tissue anchor comprises a first fabric implant that is directly attached to first and second tension members that are attached to the first tissue anchor along opposite ends thereof, wherein the first and the second tension members define a first pair of tension members, wherein when the first tissue anchor is delivered to the first papillary muscle, free ends of the first tension member and the second tension member are disposed external to the patient;

delivering a second tissue anchor to a second papillary muscle by passing the second tissue anchor through the lumen of the tissue anchor delivery catheter;

securing the second tissue anchor to the second papillary muscle, wherein the second tissue anchor comprises a second fabric implant that is directly attached to the third and the fourth tension members that are attached to the second tissue anchor along opposite ends thereof, wherein the third and fourth tension members define a second pair of tension members, wherein the first papillary muscle is located a first distance from the second papillary muscle; and tensioning at least one of the first and the second tissue anchors to cause the first papillary muscle to be spaced a second distance from the second papillary muscle, wherein the second distance is less than the first distance.

* * * * *